(12) United States Patent
Rosato

(10) Patent No.: US 11,426,098 B2
(45) Date of Patent: Aug. 30, 2022

(54) SYSTEM AND METHOD FOR GAIT MONITORING AND IMPROVEMENT

(71) Applicant: PROVA Innovations Ltd., Hamilton (CA)

(72) Inventor: Matthew Rosato, Ancaster (CA)

(73) Assignee: PROVA Innovations Ltd., Hamilton (CA)

(*) Notice: Subject to any disclaimer, the term of this patent is extended or adjusted under 35 U.S.C. 154(b) by 0 days.

(21) Appl. No.: 16/806,716

(22) Filed: Mar. 2, 2020

(65) Prior Publication Data

US 2021/0267486 A1     Sep. 2, 2021

(51) Int. Cl.
*A61B 5/11* (2006.01)
*A61B 5/00* (2006.01)

(52) U.S. Cl.
CPC ............ *A61B 5/112* (2013.01); *A61B 5/1118* (2013.01); *A61B 5/1123* (2013.01); *A61B 5/6802* (2013.01)

(58) Field of Classification Search
CPC ..... A61B 5/112; A61B 5/1118; A61B 5/1123; A61B 5/6802
See application file for complete search history.

(56) References Cited

U.S. PATENT DOCUMENTS

| | | |
|---|---|---|
| 6,769,313 B2 | 8/2004 | Weiss |
| 7,648,441 B2 | 1/2010 | Silk |
| 8,308,665 B2 | 11/2012 | Harry et al. |
| 8,858,648 B2 | 10/2014 | De Roy |
| 9,974,478 B1 * | 5/2018 | Brokaw ............... A61B 5/486 |

(Continued)

FOREIGN PATENT DOCUMENTS

| | | |
|---|---|---|
| CN | 108720841 A | 11/2018 |
| WO | 2005/094679 A1 | 10/2005 |

(Continued)

OTHER PUBLICATIONS

Crea et al., "A Wireless Flexible Sensorized Insole for Gait Analysis", Sensors, Jan. 2014, 14(1): 1073-1093.

(Continued)

*Primary Examiner* — Daniel L Cerioni
(74) *Attorney, Agent, or Firm* — Bereskin & ParrLLP/S.E.N.C.R.L., s.r.l.; Isis E. Caulder

(57) ABSTRACT

A wearable device for gait monitoring and improvement, as well as systems for sensing relevant metrics and delivering real-time sensory feedback. One system receives a baseline active training program to target a mobility abnormality; downloads it onto a wearable device; determines the activity type based on sensor data obtained from a sensor array; generates cueing intensity feedback; receives field data from the wearable device; dynamically recommends new modification parameters based on the field data; and modifies the active training program based on the new modification parameters. The system may modify cueing intensity to correct the wearer's gait by selecting ranges of values for cueing response variables for a cueing window; receiving a sample dataset from a wearable device; determining whether a number of the cycles of frames spent in a no-correction frame is increasing; adjusting the outer bounds of the no-correction frame; and adjusting the cueing window.

15 Claims, 22 Drawing Sheets

(56) References Cited

U.S. PATENT DOCUMENTS

| | | | |
|---|---|---|---|
| 2006/0022833 A1* | 2/2006 | Ferguson | A63F 13/212 |
| | | | 340/573.1 |
| 2006/0100546 A1 | 5/2006 | Silk | |
| 2007/0213126 A1* | 9/2007 | Deutsch | G07C 1/22 |
| | | | 463/36 |
| 2008/0066343 A1 | 3/2008 | Sanabria-Hernandez | |
| 2008/0108913 A1 | 5/2008 | Lengsfeld et al. | |
| 2008/0300521 A1 | 12/2008 | Karkanias et al. | |
| 2011/0145747 A1* | 6/2011 | Wong | A61B 5/7264 |
| | | | 715/771 |
| 2013/0072835 A1 | 3/2013 | Harry et al. | |
| 2016/0192862 A1 | 7/2016 | Merrell et al. | |
| 2016/0375346 A1 | 12/2016 | Czaja et al. | |
| 2017/0055880 A1 | 3/2017 | Agrawal et al. | |
| 2017/0225033 A1 | 8/2017 | Czaja | |
| 2017/0258328 A1* | 9/2017 | Dixit | A61B 5/375 |
| 2018/0220966 A1 | 8/2018 | Cohen et al. | |
| 2018/0263532 A1 | 9/2018 | Smulyan et al. | |
| 2019/0117121 A1* | 4/2019 | Kutina | A61B 5/6807 |

FOREIGN PATENT DOCUMENTS

| | | |
|---|---|---|
| WO | 2015/193856 A1 | 12/2015 |
| WO | 2017/199171 A1 | 11/2017 |
| WO | 2018/033904 A1 | 2/2018 |

OTHER PUBLICATIONS

Ma, Chapters 1-4, in "Wearable Gait Analysis Using Vision-Aided Inertial Sensor Fusion: WearGait", Master's of Applied Science in Biomedical Engineering Thesis, University of Toronto, Nov. 2016, pp. 2-29.

Ghai et al., "Role of Sonification and Rhythmic Auditory Cueing for Enhancing Gait Associated Deficits Induced by Neurotoxic Cancer Therapies: A Perspective on Auditory Neuroprosthetics", Frontiers in Neurology, Jan. 29, 2019, 10(21): 1-9.

Collins, "Vibrating insoles could aid strenuous walking and improve athletic performance", Wyss Institute, May 2, 2016, <https://wyss.harvard.edu/vibrating-insoles-could-aid-strenuous-walking-and-improve-athletic-performance> (7 pages).

Pitale et al., "A heel-strike real-time auditory feedback device to promote motor learning in children who have cerebral palsy: a pilot study to test device accuracy and feasibility to use a music and dance-based learning paradigm", Pilot and Feasibility Studies, Jan. 29, 2018, 4: 42 (7 pages).

Levine et al., eds., "Whittle's Gait Analysis", 5th Ed., Elsevier Ltd., 2012, pp. 2 & 32-33.

International Search Report and Written Opinion dated May 26, 2021 in International Patent Application No. PCT/CA2021/050238 (7 pages).

* cited by examiner

SYSTEM AND METHOD FOR GAIT MONITORING AND IMPROVEMENT

FIELD

Various embodiments are described herein that generally relate to a wearable device for gait monitoring and improvement, as well as the methods and systems for sensing relevant metrics and delivering feedback based thereon.

BACKGROUND

The following paragraphs are provided by way of background to the present disclosure. They are not, however, an admission that anything discussed therein is prior art or part of the knowledge of persons skilled in the art.

Cerebral palsy (CP) is the most common childhood disability affecting over 17 million individuals worldwide. CP is an acquired brain injury that occurs in the developing brain and affects muscle coordination and tone. A similar injury can also occur in adults but is labelled as a stroke. Surprisingly, adults are often seen to make a partial to full recovery. We do not see this in children. Instead their locomotive function seems to be locked in by the age of 5.

Unlike an adult, a child has no baseline as to what normal movement or walking feels like. They have yet to develop the cognitive awareness to understand the goals of therapy. At home, they learn to walk, making abnormal movements to compensate for their lack of tone (e.g., the classic CP scissoring gait). As the child repeats the same movements, the movements ultimately become hardwired in the developing brain. Muscle tone and spasticity can change as the child ages, but the abnormal movements remain, leading to poor lifelong habits. Yet we can observe a skilled clinician correct a child's gait in a clinical setting, only to see the child revert to old habits once they return home.

There is a need for a wearable device for gait monitoring and improvement and use thereof that address the challenges and/or shortcomings described above.

SUMMARY OF VARIOUS EMBODIMENTS

Various embodiments of a wearable device for gait monitoring and improvement, system and methods of use thereof, and computer products for use therewith, are provided according to the teachings herein.

According to one aspect of the invention, there is disclosed a method for using real-time sensory feedback on a wearable device to correct a patient's gait, the wearable device comprising a microcontroller, a sensor array, a cueing array, and a data store, the method comprising: receiving a first data file comprising a baseline active training program to target a mobility abnormality, an active training program comprising an activity type having activity properties defining criteria needed to be met to establish the activity type, and a behavior modification scheme comprising modification parameters defined by the activity type and a performance target; downloading the baseline active training program and the behavior modification scheme onto the data store; receiving sensor data from the sensor array; determining the activity type based at least in part on the sensor data and the activity properties; generating cueing intensity feedback by the microcontroller via the cueing array based at least in part on the sensor data, the performance target, and the activity type; receiving field data from the wearable device generated by the microcontroller; dynamically generating new modification parameters based at least in part on the field data, an analysis of the field data with regards to the activity type, and the performance target; and modifying the active training program based at least in part on the new modification parameters.

In at least one embodiment, the analysis of the field data further comprises determining whether the mobility abnormality improved during use of the initial training program in relation to the performance target.

In at least one embodiment, the cueing array comprises a plurality of cueing devices including a first cueing device and a second cueing device, the first cueing device having a first position and a first type being one of a lighting device, an auditory device, or a haptic device, the second cueing device having a second position and a second type being one of a lighting device, an auditory device, or a haptic device.

In at least one embodiment, the first type is different from the second type.

In at least one embodiment, the microcontroller is further configured to generate the cueing intensity feedback by the plurality of cueing devices on the cueing array based at least in part on the first type and the first position of the first cueing device, the second type and the second position of the second cueing device, and the baseline active training program.

In at least one embodiment, the microcontroller is further configured to generate the cueing intensity feedback by the plurality of cueing devices on the cueing array based at least in part on cueing vector placement comprising dividing cueing vectors into zones and selecting the cueing vectors to provide the cueing intensity feedback corresponding to the behavior modification scheme.

In at least one embodiment, the activity properties comprise at least one of changes in height, walking cadence parameters, or running cadence parameters.

In at least one embodiment, the first data file further comprises at least one of a clinician assessment data file relating to the patient's gait and a statistical gait assessment file.

In at least one embodiment, the method further comprises generating a recommended training program based at least in part on the clinician data.

In at least one embodiment, the activity type is one of walking, running, ambulating with a mobility aid, going up/down an incline, ascending/descending stairs, idling, performing a custom movement, performing a specialized movement, performing an unknown movement, or transitioning from one activity type to another activity type.

In at least one embodiment, the criteria is a set of data specific to the activity type sufficient to establish the activity type, the data including at least one of position, velocity, or acceleration.

In at least one embodiment, the method further comprises tuning the cueing intensity feedback by the microcontroller based at least in part on a comparison of the sensor data with the performance target.

In at least one embodiment, the method further comprises receiving clinical trial data from the wearable device based at least in part on the cueing intensity feedback.

In at least one embodiment, the method further comprises receiving device node data from a device node that is associated with a different body part than the wearable device, where the device node data is related to measurements of movement of the different body part.

In at least one embodiment, generating the cueing intensity feedback is further based on the device node data, and the method further comprises transmitting the cueing intensity feedback to the device node.

In another aspect, there is provided a method for modifying cueing intensity to correct a patient's gait comprising: selecting ranges of values for one or more cueing response variables for a cueing window; receiving a sample dataset from a wearable device; determining the existence of a cycle in a no correction frame, the no correction frame having outer bounds bordering a first of one or more degree of correction frames; determining a proportion of cycles of frames spent in each of the one or more degree of correction frames; determining a first condition of whether a number of the cycles of frames spent in the no correction frame is increasing; adjusting the outer bounds of the no correction frame based at least in part on the first condition; and providing a recommendation to adjust the ranges of values for the one or more cueing response variables for the cueing window.

In another aspect, there is provided a method for determining an activity type and performing cueing to correct a patient's gait comprising: receiving gait parameters for a patient, the gait parameters comprising at least one of physical parameters, temporal parameters, spatial parameters, and clearance parameters; initiating a step count program based at least in part on the gait parameters; receiving activity-related data; receiving first sensor data from a wearable device, the first sensor data comprising measured data relating to at least one of the gait parameters; processing the first sensor data to generate processed sensor data; evaluating an extent of changes measured by the wearable device based at least in part on the processed sensor data; determining the activity type for the wearable device based at least in part on the processed sensor data and the extent of changes, the activity type comprising at least one of walking movement, running movement, ramp movement, stair movement, and specialized movement; and performing cueing based on the activity type.

In at least one embodiment, the method further comprises measuring response to the cueing based at least in part on subsequently received sensor data.

In at least one embodiment, the activity type is one of walking, running, walking with a cane or mobility aid, going up a ramp, going down a ramp, climbing stairs, going down stairs, transitioning between one activity type to another activity type, or a custom activity type.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1:
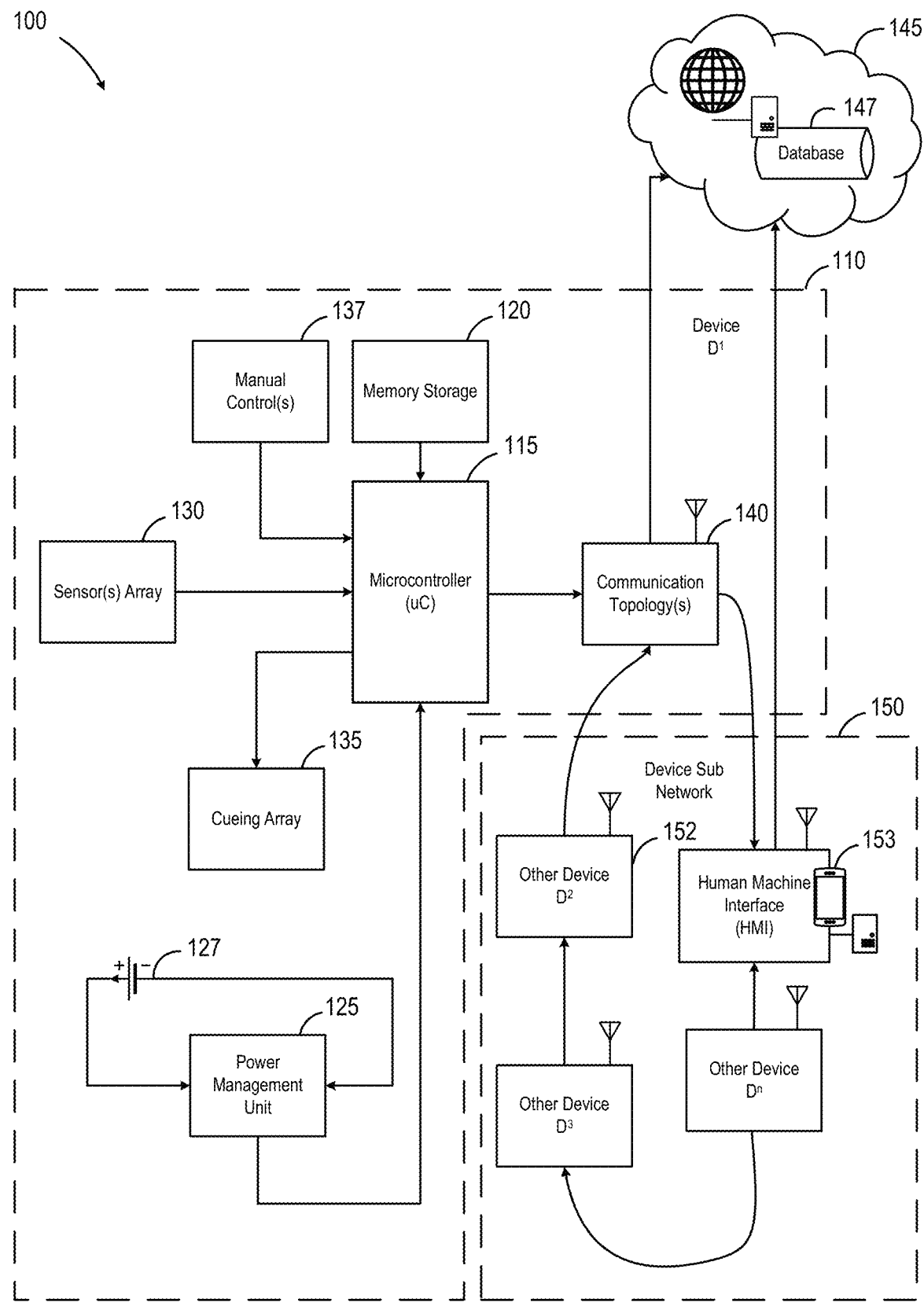
FIG. 1 shows a block diagram of an example embodiment of a system for gait monitoring and improvement.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems, or methods having all of the features of any one of the devices, systems, or methods described below or to features common to multiple or all of the devices, systems, or methods described herein. It is possible that there may be a device, system, or method described herein that is not an embodiment of any claimed subject matter. Any subject matter that is described herein that is not claimed in this document may be the subject matter of another protective instrument, for example, a continuing patent application, and the applicants, inventors, or owners do not intend to abandon, disclaim, or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures, and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical or electrical connotation. For example, as used herein, the terms coupled or coupling can indicate that two elements or devices can be directly connected to one another or connected to one another through one or more intermediate elements or devices via an electrical signal, electrical connection, or a mechanical element depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5%, or 10%, for example, if this deviation does not negate the meaning of the term it modifies.

Furthermore, the recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

The example embodiments of the devices, systems, or methods described in accordance with the teachings herein may be implemented as a combination of hardware and software. For example, the embodiments described herein may be implemented, at least in part, by using one or more computer programs, executing on one or more programmable devices comprising at least one processing element and at least one storage element (i.e., at least one volatile memory element and at least one non-volatile memory element). The hardware may comprise input devices including at least one of a touch screen, a keyboard, a mouse, buttons, keys, sliders, and the like, as well as one or more of a display, a printer, and the like depending on the implementation of the hardware.

It should also be noted that there may be some elements that are used to implement at least part of the embodiments described herein that may be implemented via software that is written in a high-level procedural language such as object oriented programming. The program code may be written in C++, C#, JavaScript, Python, or any other suitable programming language and may comprise modules or classes, as is known to those skilled in object-oriented programming. Alternatively, or in addition thereto, some of these elements implemented via software may be written in assembly language, machine language, digital logic, discrete circuit level components, or firmware as needed. In either case, the language may be a compiled or interpreted language.

At least some of these software programs may be stored on a computer readable medium such as, but not limited to, a ROM, a magnetic disk, an optical disc, a USB key, and the like that is readable by a device having a processor, an operating system, and the associated hardware and software that is necessary to implement the functionality of at least one of the embodiments described herein. The software program code, when read by the device, configures the device to operate in a new, specific, and predefined manner (e.g., as a specific-purpose computer) in order to perform at least one of the methods described herein.

At least some of the programs associated with the devices, systems, and methods of the embodiments described herein may be capable of being distributed in a computer program product comprising a computer readable medium that bears computer usable instructions, such as program code, for one or more processing units. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g., downloads), media, digital and analog signals, and the like. The computer useable instructions may also be in various formats, including compiled and non-compiled code.

In accordance with the teachings herein, there are provided various embodiments for a wearable device for gait monitoring and improvement, system and methods of use thereof, and computer products for use therewith.

There are technical challenges to providing a device or system to allow a person in need of having their gait monitored and/or corrected, such as a child with CP, outside the clinic. The example embodiments that are described below provide technical solutions to these challenges. The example embodiments: (a) allow the person to take the therapy with them outside the clinic; (b) utilize neuroplasticity—the brain's ability to reorganize to its advantage; and/or (c) provide the person with real-time feedback, allowing them to self-correct improper movements, thus reinforcing good lifelong habits.

In at least one embodiment, the device is a wearable outer sole that measures the foot's position and delivers haptic or sensory feedback. It does this through the use of small embedded motors, LEDs, and audio drivers. If a child's movement tracks outside of a clinician's setpoint, the device delivers cueing in the form of at least one of small vibratory sensations, audio, and light, that guide the child back to a more normal trajectory or position. For example, the cueing can be just lighting with no audio or vibration, or all three of vibration, audio, and light (not necessarily at the same time).

Similar to how lane departure warns a driver in an automobile that he is veering from the lane, the device delivers haptic, lighting, and auditory cues to guide a child's movements through each aspect of the gait cycle. The child's healthcare provider will have insight to the child's behavior at home and will be able to analyze statistics and quantify the child's response. It will be appreciated that the device can be adapted for adults with mobility issues (e.g., stroke patients) and able-bodied athletes seeking to improve performance.

Different embodiments may have variations in form factor, including an inner sole as well as parts that can be directly fitted into a child's orthotic, or into the sole of a shoe itself. The device's functionality is also not limited to the foot, but can be expanded in scope to include other body parts or all aspects of guided muscle movement.

At least one embodiment described in accordance with the teachings herein provides technical solutions via at least one of: (a) providing real-time feedback; (b) building a neuro-learning-network into the device, meaning that as more patients use the device, aggregate statistics can be gathered and applied; and (c) building synaptic connections in the brain in conjunction with or instead of building muscle.

In at least one embodiment, a system for gait monitoring and improvement is provided to be used with a wearable device. The wearable device is either incorporated or worn over the shoe, on the foot, or incorporated into an orthotic. The device is comprised of vibratory motors, a speaker, lights (LEDs), a position recording device (e.g., an MPU), pressure sensors, proximity sensors, a microcomputer, and various supportive electronics including wireless transmission. Data is sent to a cloud-based system for analysis. The system responds to the position of the foot and delivers various frequencies of sensory response (e.g., touch, sight, sound) depending on deviation from norms. The cloud-based system records data and uses a neural network to learn responses individualized to each patient.

Reference is first made to FIG. 1, showing a block diagram of an example embodiment of a system 100 for gait monitoring and improvement. System 100 has a power management unit 125 that provides electrical and/or other (e.g., electro-mechanical) power to one or more devices and/or connections of the system 100. The power management unit 125 can receive its power from a battery 127 or other power source. The power management unit 125 may include battery management functionality and protection such as short circuit, over-discharge, overcurrent protection, constant current charging, or constant voltage charging. The power management unit 125 directs power to a wearable device 110. The wearable device 110 comprises a microcontroller 115.

The microcontroller 115 is coupled (e.g., electrically) to a data store 120, a sensor array 130, a cueing array 135, manual controls 137, and a network interface 140. The microcontroller 115 may include, for example, an application-specific integrated circuit (ASIC), a field programmable gate array (FPGA), system-on-chip (SoC), or other suitable electrical or electronic component. The data store 120 includes a non-transitory computer-readable storage medium. The network interface 140 provides a connection to a cloud 145 and a device subnetwork 150. The cloud 145 can be, for example, an offsite server that serves a database 147 and a neural network. The cloud 145 may be connected to a human-machine interface (HMI) 153. The device subnetwork 150 may include the HMI 153 and other devices 152. The other devices may be, for example, electronic or electro-mechanical devices attached to or near the body (or clothing) of the person being monitored (e.g., a patient) or on items the patient interacts with such as mobility devices and aids.

The power management unit 125 may monitor power connections and battery charges, shut down unnecessary system components when left idle, control sleep and power functions (e.g., on and off), and initiate a power conservation mode. The power conservation mode may, for example, be initiated when the level of the battery 127 drops below a certain threshold, at which time operation of the cueing array 135 may be altered (e.g., with less power, less cueing) to allow for longer runtime.

The cueing array 135 includes circuitry that provides signals (e.g., electronic) to cueing elements, such as light-emitting diodes (LEDs), vibratory motors, and speakers. Alternatively, or in addition, the cueing elements include actuation-type motors or other mechanical or electro-mechanical devices that provide haptic feedback.

In at least one embodiment, the system 100 has a calibrator (e.g., a calibration module, chip, circuitry, or logic) that allows calibration of one or more of the components of the system 100 to be done in the field. The calibrator may be, for example, loaded onto, connected to, or incorporated into the microcontroller 115.

Figure 2:
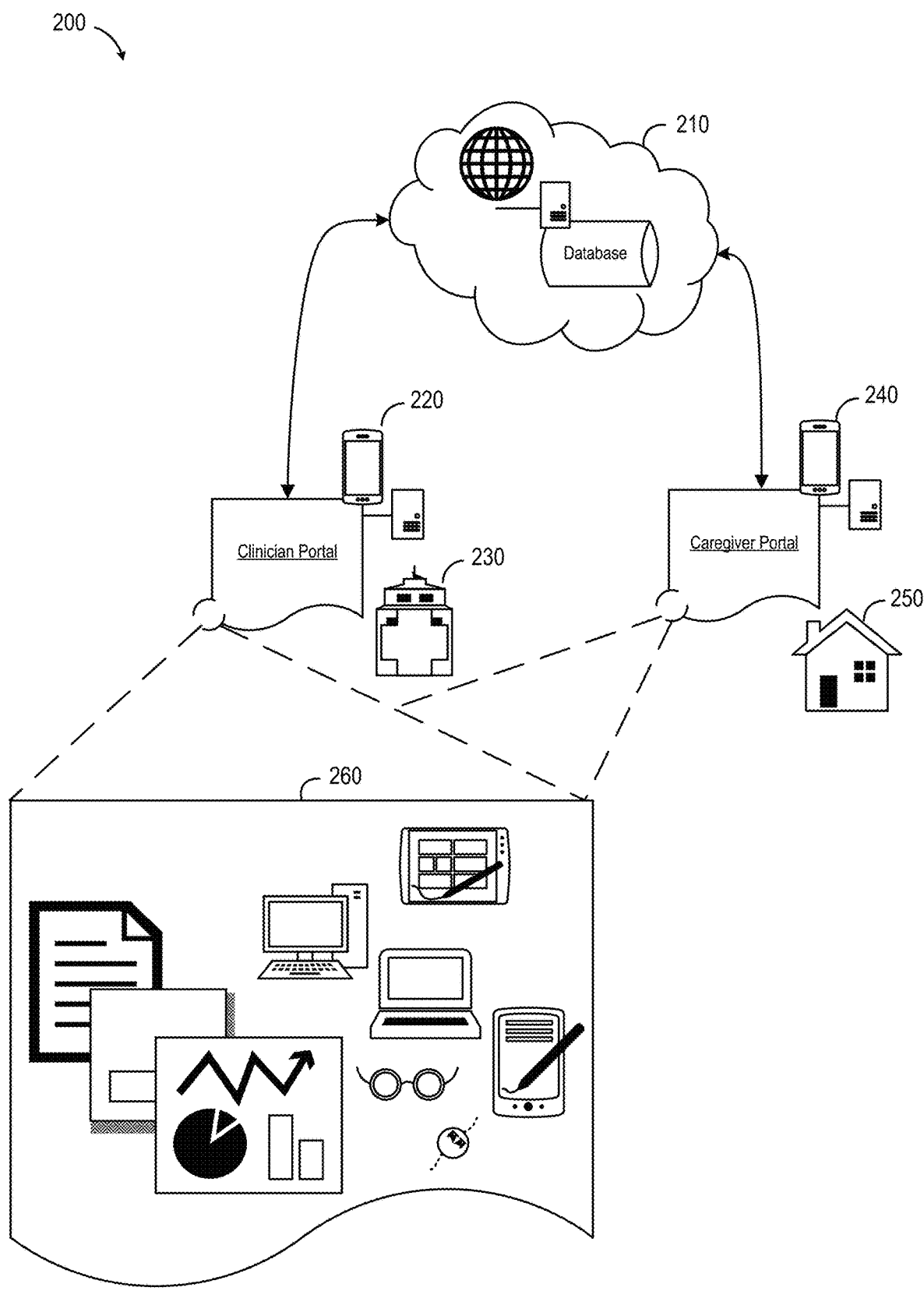
FIG. 2 shows a block diagram of an example embodiment of a cloud network for use with a system for gait monitoring and improvement.

Referring now to FIG. 2, shown therein is a block diagram of an example embodiment of a cloud network 200 for use with a system for gait monitoring and improvement. Some or all of the cloud network 200 may be an implementation of the cloud 145 for use with the system 100.

The cloud network 200 includes a cloud 210 (or similar communications system) that has the ability to transmit to and receive from a clinician portal 220 and a caregiver portal 240. Either or both portals may be displayed, for example, on a mobile device or personal computer, which together (or separately) can be used as the HMI 153 of system 100.

The clinician portal 220 can be connected to a clinic server 230. The clinic server 230 may be the computers, networks, and/or communications interfaces in a private clinic, a clinic within a hospital, a hospital department, an entire hospital, or a hospital network, for example. The caregiver portal 240 can be connected to a caregiver server 250. The caregiver server 250 may be the computers, networks, and/or network interfaces in a caregiver setting, a home, a residence, a gym, or a training facility, for example. Each of both of the clinician portal 220 and the caregiver portal 240 can be connected to an HMI 260. The HMI 260 may be a computing device, such as a laptop, a mobile phone, tablet, smart watch, or smart glasses, that provides input from and/or output to a human.

The cloud 210 can be coupled (e.g., electronically) to a database and a server for processing and data mining. The database may be the database 147 of system 100. The cloud network 200 can be, for example, the Internet over the world wide web.

In at least one embodiment, various elements of the system 100 are configured to send, receive, and/or process data. The data may be in any form that can be sent, received, interpreted, stored, or executed, such as a signal, an electromagnetic wave, binary digits, a data point, a packet, a record, a data set, a file, executable code, or a portion of a database. For example, input into a clinician portal 220 may be received from a clinician's mobile device, sent to the cloud 210, stored on the database 147, then processed by the clinic server 230 to generate a training program to load onto the microcontroller 115, which when executed actuates a cueing element. In this example, the data involved at the various stages is converted from one form to another as needed. For the embodiments described herein, any reference to data can be likewise interpreted as having the form most suitable for its use.

Figure 3:
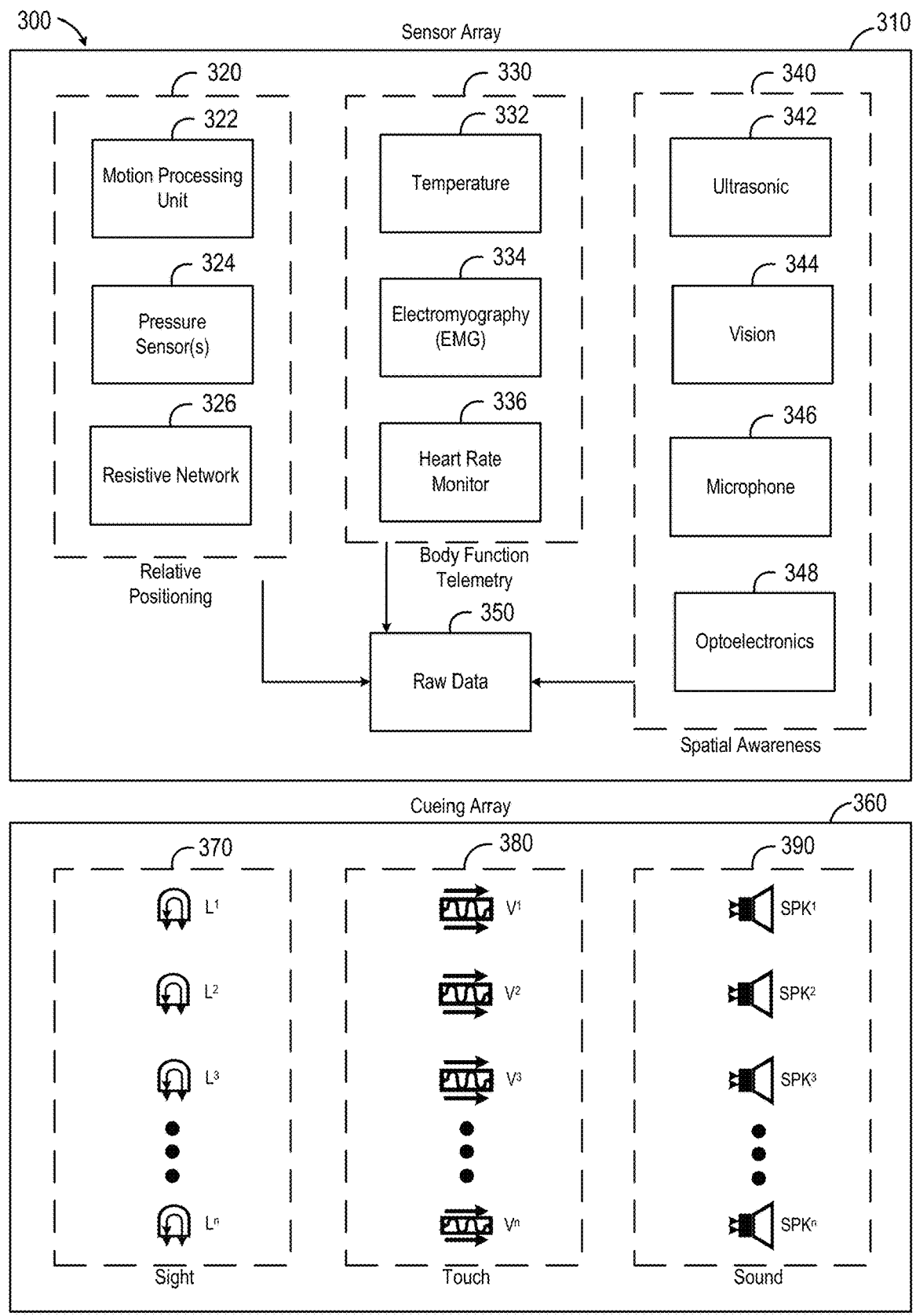
FIG. 3 shows a block diagram of an example embodiment of sensor and cueing networks for use with a system for gait monitoring and improvement.

Referring now to FIG. 3, shown therein is a block diagram of an example embodiment of sensor and cueing networks 300 for use with a system for gait monitoring and improvement. The sensor and cueing networks 300 include a sensor array 310 and a cueing array 360. Some or all of the sensor array 310 may be an implementation of the sensor network 130 for use with the system 100. Some or all of the cueing array 360 may be an implementation of the cueing array 135 for use with the system 100.

The sensor array 310 includes a relative positioning module 320, a body function telemetry module 330, a spatial awareness module 340, and raw data store 350. The positioning module 320 includes a motion processing unit (MPU) 322, one or more pressure sensors 324, and a resistive network 326. The MPU 322 has three-dimensional (e.g., xyz direction) capabilities for various parameters. The MPU 322 may include one or more of: a magnetometer, a gyro, an accelerometer, a tachometer, a temperature sensor, a barometer, a clock, a wireless chipset, and a GPS receiver. The magnetometer can, for example, measure changes in magnetic fields. The gyro can, for example, measure changes in motion. The accelerometer can, for example, measure acceleration. The tachometer can, for example, measure rotational speed. The temperature sensor can, for example, measure the temperature of the electronics for calibration. The barometer can, for example, measure air pressure. The clock can, for example, measure time. The wireless chipset can, for example, triangulate the device's position. The GPS receiver can, for example, be capable of receiving information from GPS satellites used to calculate the device's position. The body function telemetry module 330 may include a thermostat 332, an electromyograph (EMG) 334, and a heart rate monitor 336. The spatial awareness module 340 may include an ultrasound sensor 342, a vision sensor 344, a microphone 346, and optoelectronics 348. The raw data store 350 is a data storage device capable of storing (and optionally formatting) the data generated by some or all of the components of the sensor array 310.

In at least one implementation, one or more of the modules may provide data that can be used to monitor progress of the patient. For example, the heart rate monitor 336 may provide data relating to energy use or conservation, which may be relevant to progress or improvement in gait for patients.

The cueing array 360 includes circuitry that provides signals (e.g., electronic) to cueing elements. The cueing elements may include light-emitting diodes (LEDs) 370, vibratory motors 380, and speakers 390. LEDs 370 can stimulate sight, vibratory motors 380 can stimulate touch, and speakers 390 can stimulate hearing.

Figure 4:
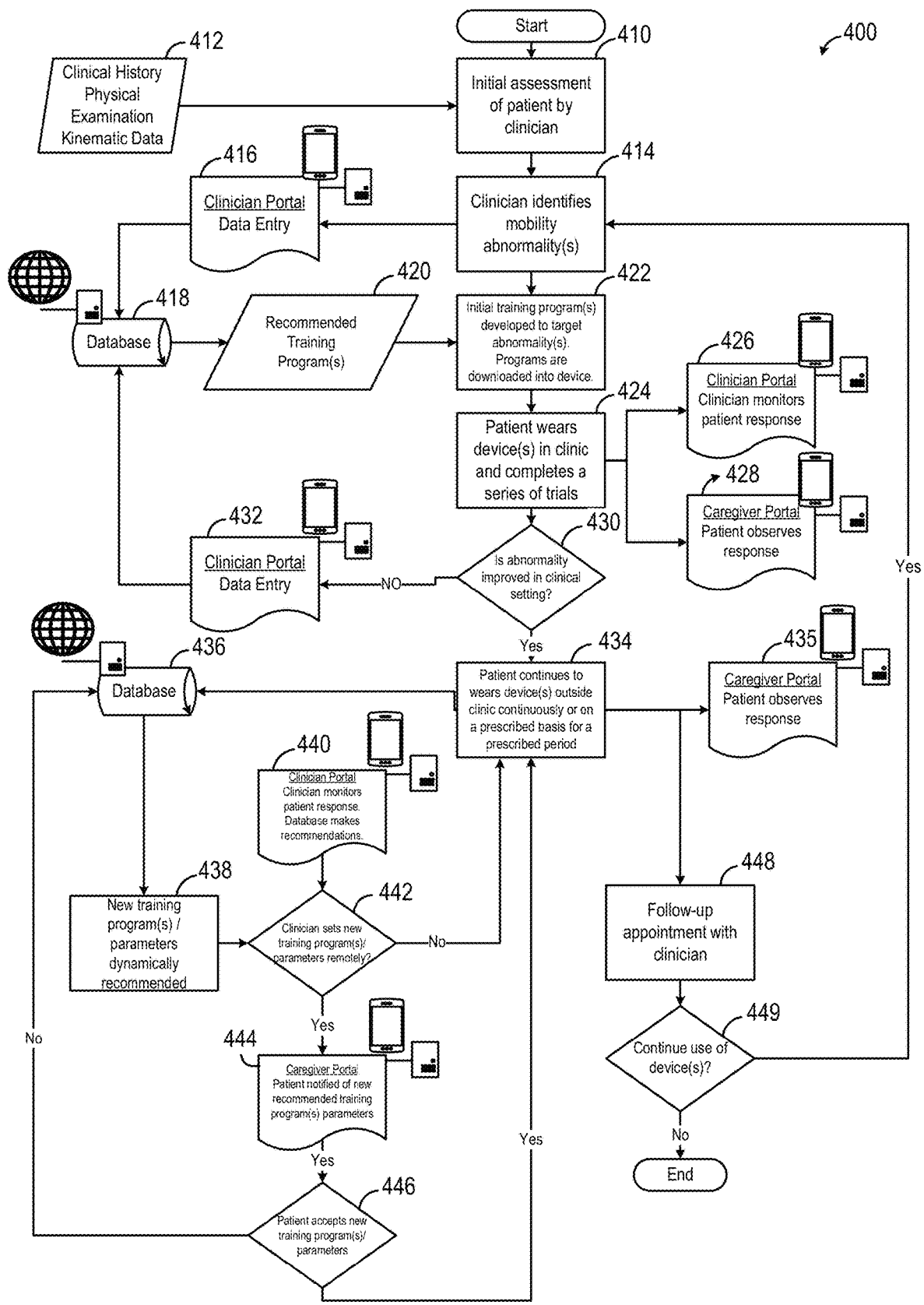
FIG. 4 shows a flow chart of an example embodiment of a method of gait monitoring and improvement.

Referring now to FIG. 4, shown therein is a flow chart of an example embodiment of a method 400 of gait monitoring and improvement.

Some or all of method 400 can be used to provide a process from initial assessment to training with the wearable device 110 outside of the clinic to delivering and storing metrics in the database 147. Method 400 may be carried out, for example, by system 100.

At 410, the system 100 receives data corresponding to an initial assessment of a patient by a clinician. Alternatively, or in addition, the system 100 may make the initial assessment with some or no input from the clinician. The initial assessment may be based on a clinical history file, a physical examination file, and/or kinematic data.

At 412, the system 100 receives at least one of a clinical history file, a physical examination file, and kinematic data. The physical examination file, for example, may contain data generated by a skilled practitioner. Alternatively, or in addition, the clinician may receive related files and/or data through a clinician portal.

At 414, the system 100 receives a report from the clinician that identifies mobility abnormalities. Alternatively, or in addition, the system 100 may generate the report with some or no input from the clinician. The report may include a hypothesis of the cause(s) of abnormalities.

At 416, the system 100 receives clinician data entered from the clinician portal. The clinician portal may be, for example, the clinician portal 220 on cloud network 200.

At 418, the system 100 stores the clinician data into the database 147.

At 420, the system 100 generates a recommended training program based at least in part on data stored in the database 147.

At 422, the system 100 develops an initial training program (or multiple programs) to target the identified mobility abnormalities. The system 100 may download the initial training program onto a device on the system 100, thereby becoming an active training program. The device may be, for example, the wearable device 110. Alternatively, or in addition, the device may be other devices 152 that can be, for example, worn by or attached to the patient.

At 424, the system 100 receives data from the device worn by the patient in the clinic while completing a series of trials. The system 100 may, for example, receive cueing intensity feedback, monitor the patient's gait, and monitor any improvement. The system 100 generates an output (e.g., in real time) of the data (modified or unmodified) from the device and/or the patient's response.

At 426, the system 100 sends the generated output (e.g., in real time) to the clinician portal. The clinician can monitor the patient's response from the clinician portal.

At 428, the system 100 sends the generated output (e.g., in real time) to a caregiver portal. The caregiver portal may be, for example, the caregiver portal 240 on cloud network 200. The patient (or caregiver) can observe their response from the caregiver portal.

At 430, the system 100 determines whether the abnormality improved in the clinical setting. If Yes (i.e., the abnormality improved in the clinical setting), then the method proceeds to 434. If No (i.e., the abnormality did not improve in the clinical setting), then the method 400 proceeds to 432.

At 432, the system 100 receives data from the clinician portal. This data may be clinical data or other data to be sent to the database 147, for example, to assist in future training program recommendations. Optionally, the system 100 indicates on the clinician portal that the abnormality did not improve in the clinical setting. Also optionally, the system 100 provides a data entry prompt on the clinician portal.

At 434, the system 100 receives data from the device worn by the patient outside the clinic. The data (also known as "field data") may be generated by sensors on the device while the device is worn continuously or on a prescribed basis for a prescribed period. The system 100 may, for example, receive cueing intensity feedback, monitor the patient's gait, and monitor any improvement. The system 100 generates an output of the data (modified or unmodified) from the device. The output may be generated, for example, in real time, periodically, in batches, or in a consolidated format.

At 435, the system 100 sends the generated output to the caregiver portal. The patient (or caregiver) can observe their response from the caregiver portal.

At 436, the system 100 sends the generated output to the database 147.

At 438, the system 100 dynamically recommends new training programs/parameters based at least in part on the (updated) data from the database 147. The dynamic recommendation may be, for example, instantaneous, in real time, using push technology, or using pull technology.

At 440, the system 100 receives data from the clinician portal. This data may be clinical data or other data related to the patient's response, for example. Optionally, the system 100 provides a data entry prompt on the clinician portal.

At 442, the system 100 determines whether to set a new training program or parameters remotely. This determination may be, for example, automatically determined by the system 100 or set directly by the clinician. If Yes (i.e., set a new training program or parameters remotely), then the method proceeds to 444. If No (i.e., do not set a new training program or parameters remotely), then the method 400 returns to 434.

At 444, the system 100 sends the new recommended training program parameters to the caregiver portal. The system 100 may provide a data entry prompt on the caregiver portal, for example, whether to accept the new parameters.

At 446, the system 100 receives notification of whether or not to accept the new training program(s)/parameters from the caregiver portal. If Yes (i.e., accept the new training program(s)/parameters), then the method returns to 434. If No (i.e., not to accept the new training program(s)/parameters), then the method returns to 436.

At 448, the system 100 provides a notification (e.g., on the device, the clinician portal, the caregiver portal) to make a follow-up appointment with the clinician.

At 449, the system 100 determines whether continued use of the device is selected. Alternatively, or in addition, continued of the use of the device may be requested, permitted, or allowed, depending on such factors as whether the option is given on the clinician portal or the caregiver portal, or whether it is automatically determined (for example, on the device itself). If Yes (i.e., continued use of the device is selected), then the method 400 returns to 414. If No (i.e., continued use of the device is not selected), then the method 400 ends.

In at least one embodiment, the method 400 is stored as a plurality of instructions on a non-transitory computer-readable medium that is executable by a processor of a system for adapting the system to implement the method 400. The system may be system 100, where, for example, the non-transitory computer-readable medium is data store 120 and the processor is microcontroller 115.

Figure 5:
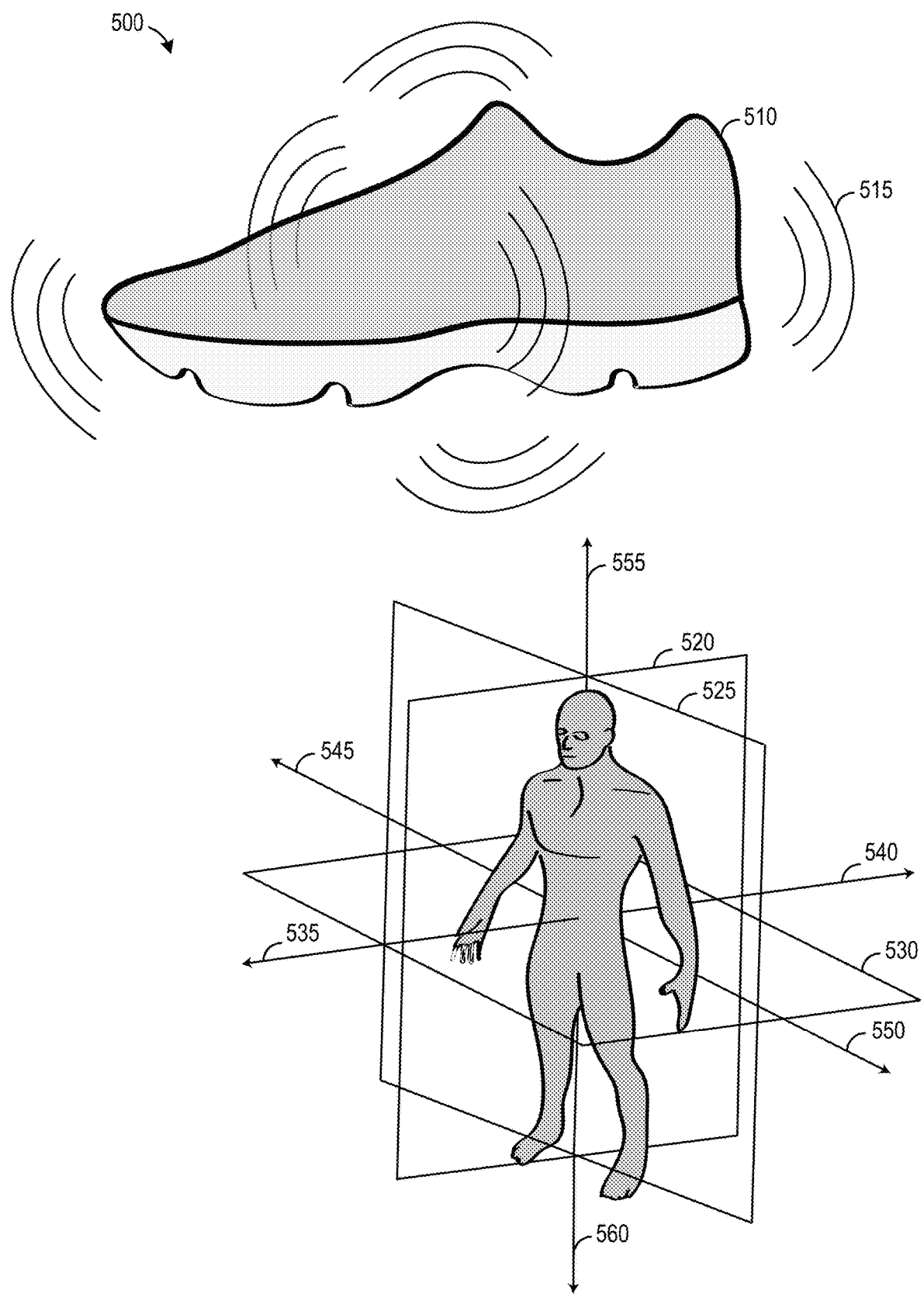
FIG. 5 shows a schematic diagram of an example of cueing device cueing planes and directions for gait monitoring and improvement.

Referring now to FIG. 5, shown therein is a schematic diagram of an example of cueing device cueing planes and directions 500 for gait monitoring and improvement.

Cueing devices are situated on a wearable device 510 to give feedback 515 to each anatomical position across three reference planes and six fundamental directions. The cueing devices may include, for example, lights, speakers, and vibratory motors.

The six fundamental directions are: left 550, right 545, superior 555, inferior 560, anterior 535, and posterior 540. The superior 555 and inferior 560 directions can also be thought of as up and down. The anterior 535 and posterior 540 directions can also be thought of as front and back.

The three reference planes are the sagittal plane 520, the transverse plane 530, and the frontal plane 525. The sagittal plane 520 divides the left side of the body and the right side of the body. The transverse plane 530 divides the upper body and the lower body. The frontal plane 525 divides the front of the body and the rear of the body.

Each of the reference planes has its corresponding pair of fundamental directions to which it is orthogonal. The sagittal plane 520 is orthogonal to the left 550 and right 545 directions. The transverse plane 530 is orthogonal to the superior 555 and inferior 560 directions. The frontal plane 525 is orthogonal to the anterior 535 and posterior 540 directions.

Figure 6:
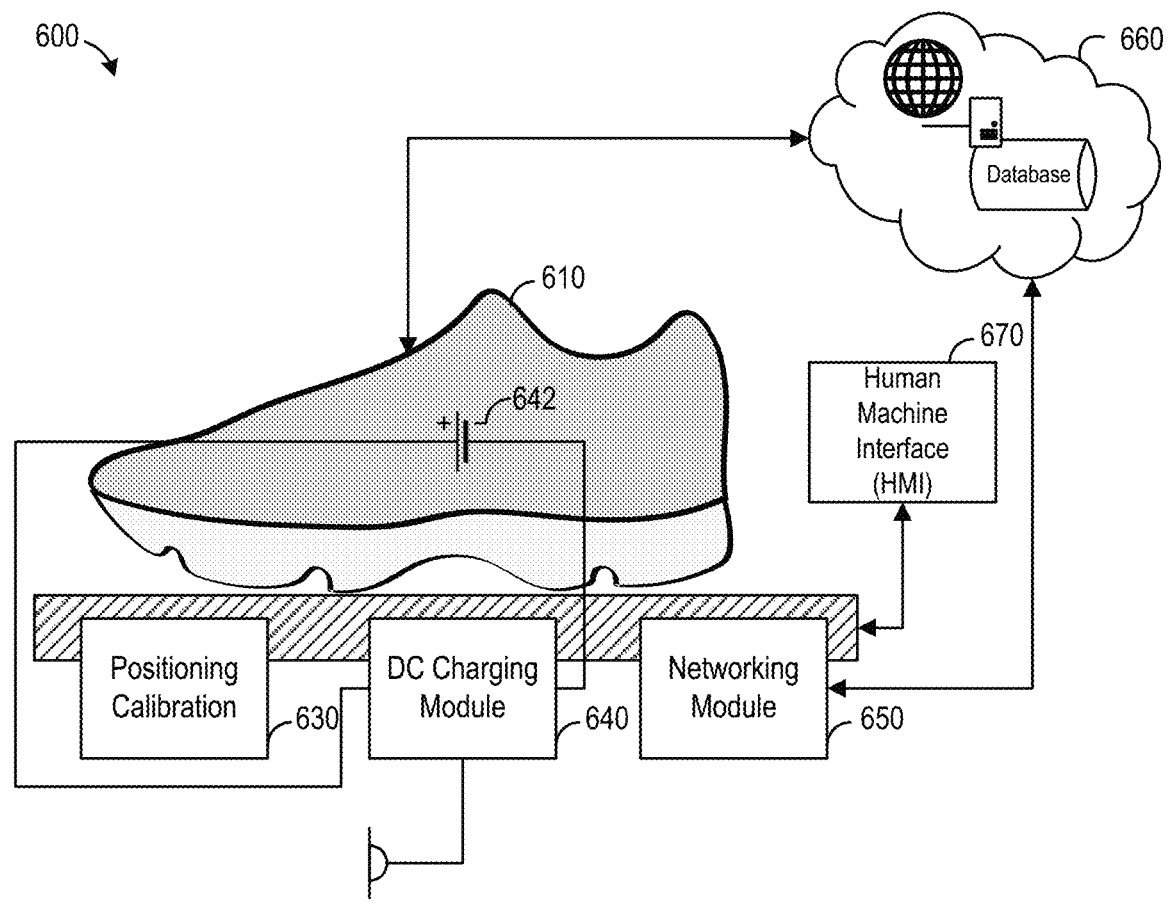
FIG. 6 shows a schematic diagram of an example embodiment of a docking station for a wearable device for gait monitoring and improvement.

Referring now to FIG. 6, shown therein is a schematic diagram of an example embodiment of a docking station 600 for a wearable device for gait monitoring and improvement.

The docking station 600 can provide one or more functions related to the operation of the wearable device 610. The device 610 may be a shoe with the system 100 integrated therewith. Alternatively, the device 610 is a removable accessory (e.g., removable from a shoe, orthotic, walking boot, brace, etc., using Velcro, clips, buckles, straps, magnets, etc.) in which the system 100 is housed. The docking station 600 may include a module for positioning calibration 630. The docking station 600 may include a DC charging module 640 that can recharge the battery 620 of the device 610. The DC charging module 640 may receive power, for example, from an electric power source 642 and may include a protection circuit. The docking station 600 may include a networking module 650 to provide network connectivity between the device 610 and a network 660. The network 660 may be, for example, a single computer, a local area network (LAN), a portal, or the Internet. The networking module 650 may have a communications interface (wired or wireless) to send data to or receive data from the system 100. The docking station 600 may include a Human Machine Interface (HMI) module 670. The HMI module 670 may include an indicator for battery life and charge status, manual controls to control the module for positioning calibration 630, and other control functions.

Figure 7:
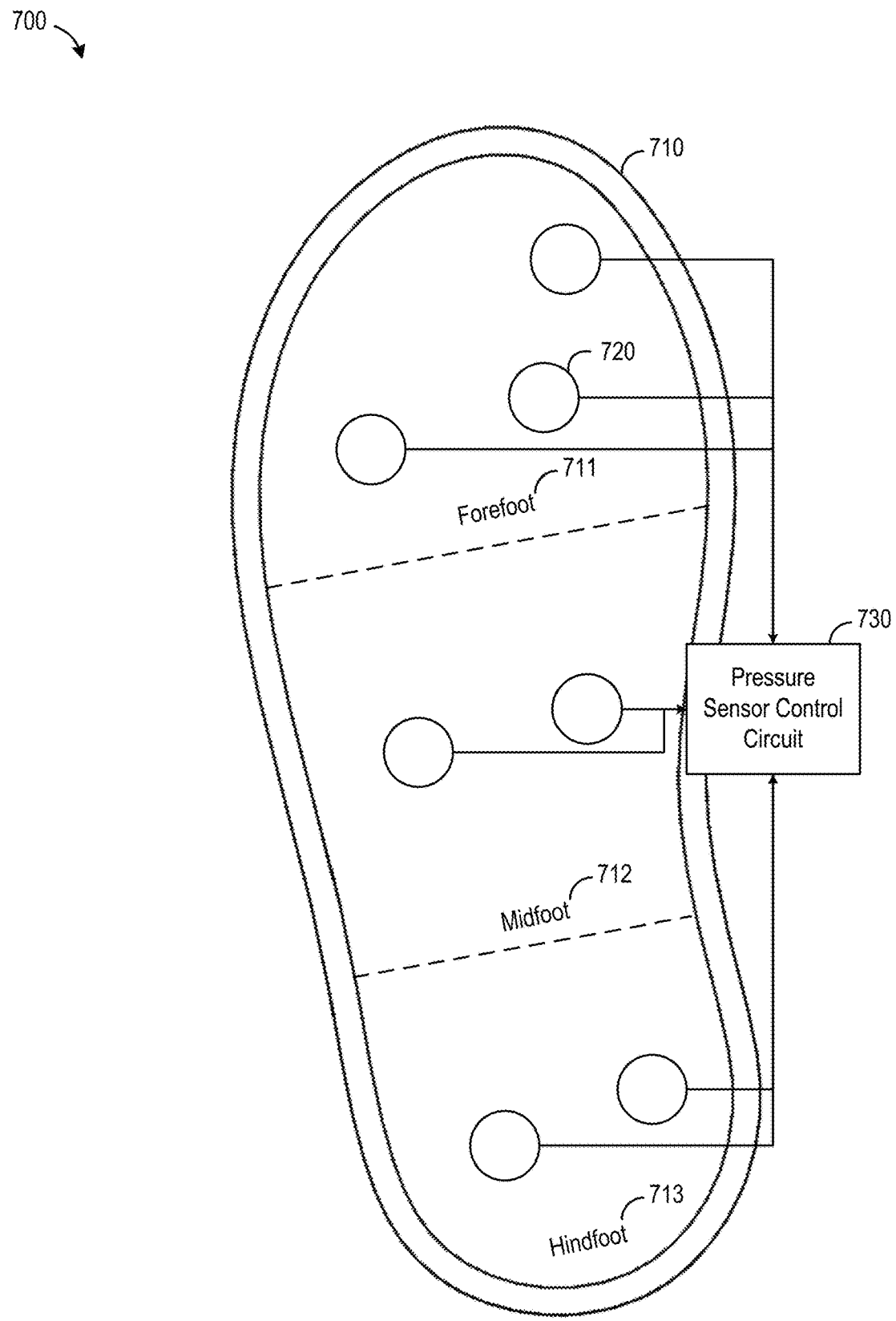
FIG. 7 shows a schematic diagram of an example of pressure sensor placement on a wearable device for gait monitoring and improvement.

Referring now to FIG. 7, shown therein is a schematic diagram of an example of pressure sensor placement 700 on a wearable device for gait monitoring and improvement. The wearable device may be the wearable device 110 of system 100.

The pressure sensor placement 700 can be divided into zones on the wearable device 710, such as the forefoot 711, the midfoot 712, and the hindfoot 713. There may be pressure sensors 720 in one, two, or all three zones. In each zone, there may be no pressure sensors, one pressure sensor, or a plurality of pressure sensors. Within each zone, there may be subzones (such as the big toe), for example, to represent particular areas of interest, or to reflect unique anatomy. The pressure sensors 720 are in electric communication with a pressure sensor control circuit 730.

For example, as shown in FIG. 7, there are three pressure sensors 720 in the forefoot 711, two pressure sensors 720 in the midfoot 712, and two pressure sensors 720 in the hindfoot 713. The pressure sensors 720 in the forefoot 711 are arranged to sense pressure on the ball of the foot and the big toe.

Figure 8A:
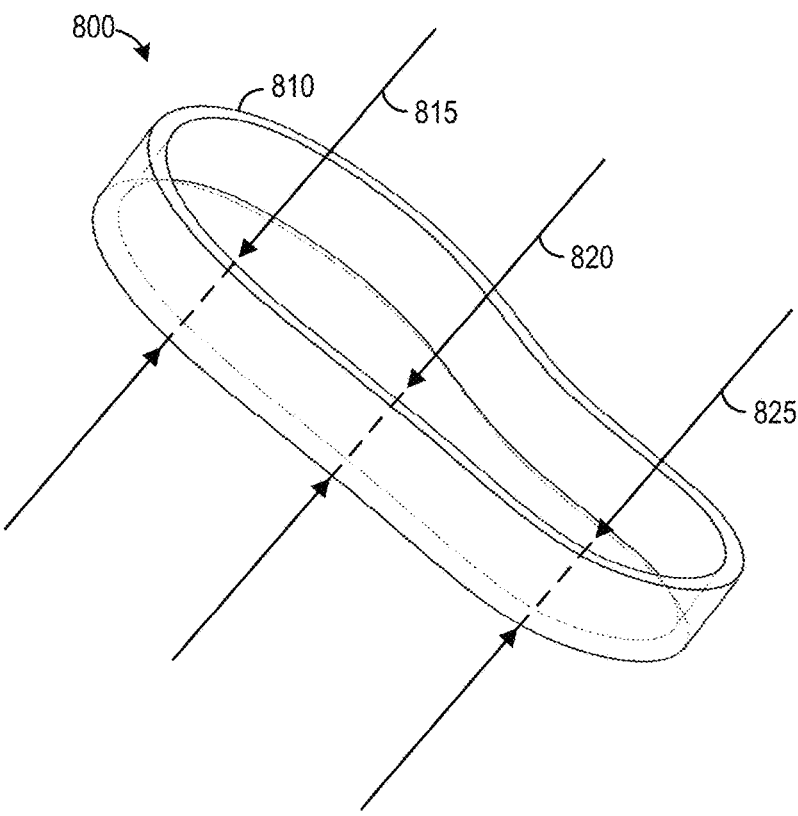
FIG. 8A shows a schematic diagram of a perspective view of an example of cueing vector placement on a wearable device for gait monitoring and improvement.
Figure 8B:
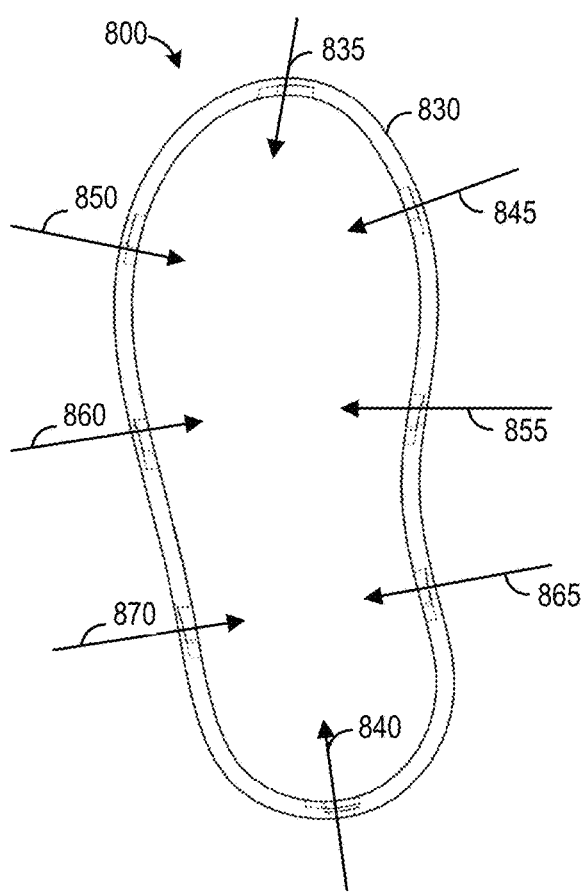
FIG. 8B shows a schematic diagram of a top view of an example of cueing vector placement on a wearable device for gait monitoring and improvement.

Referring now to FIGS. 8A and 8B, shown therein are schematic diagrams of an example of cueing vector placement 800 on a wearable device for gait monitoring and improvement. The cueing vectors may refer to one or more of vibratory motors, lights, and speakers.

The cueing vector placement 800 may be divided into zones, such as the forefoot, the midfoot, and the hindfoot. These zones may or may not be the same zones as the corresponding zones 710, 720, and 730 in FIG. 7. There may be vibratory motors, lights, and/or speakers in one, two, or all three zones. In each zone, there may be no motors, one motor, or a plurality of motors. In each zone, there may be no lights, one light, or a plurality of lights. In each zone, there may be no speakers, one speaker, or a plurality of speakers. Within each zone, there may be subzones (such as the big toe) to represent particular areas of interest, to aid in visibility, etc. The vibratory motors may or may not be paired with the lights and/or speakers.

The cueing vectors may be vertical varying between 0 to 180 degrees (e.g., superior 555 and inferior 560). For example, as shown in FIG. 8A, the wearable device 810 has vertical cueing vectors in three places. The vertical cueing vectors shown are: vertical forefoot 815, vertical midfoot 820, and vertical hindfoot 825.

The cueing vectors may be horizontal varying between 0 to 180 degrees (e.g., anterior 535, posterior 540, right 545, left 550). For example, as shown in FIG. 8B, the wearable device 830 has horizontal cueing vectors in eight places. The horizontal cueing vectors shown are: anterior forefoot 835, posterior hindfoot 840, right forefoot 845, left forefoot 850, right midfoot 855, left midfoot 860, right hindfoot 865, and left hindfoot 870.

In at least one embodiment, the cueing vectors are a combination of one or more vertical cueing vectors and one or more horizontal cueing vectors.

In at least one embodiment, the cueing vectors are on inclined planes and/or at different elevations, for example, to reflect pitch, roll, and yaw.

Figure 9:
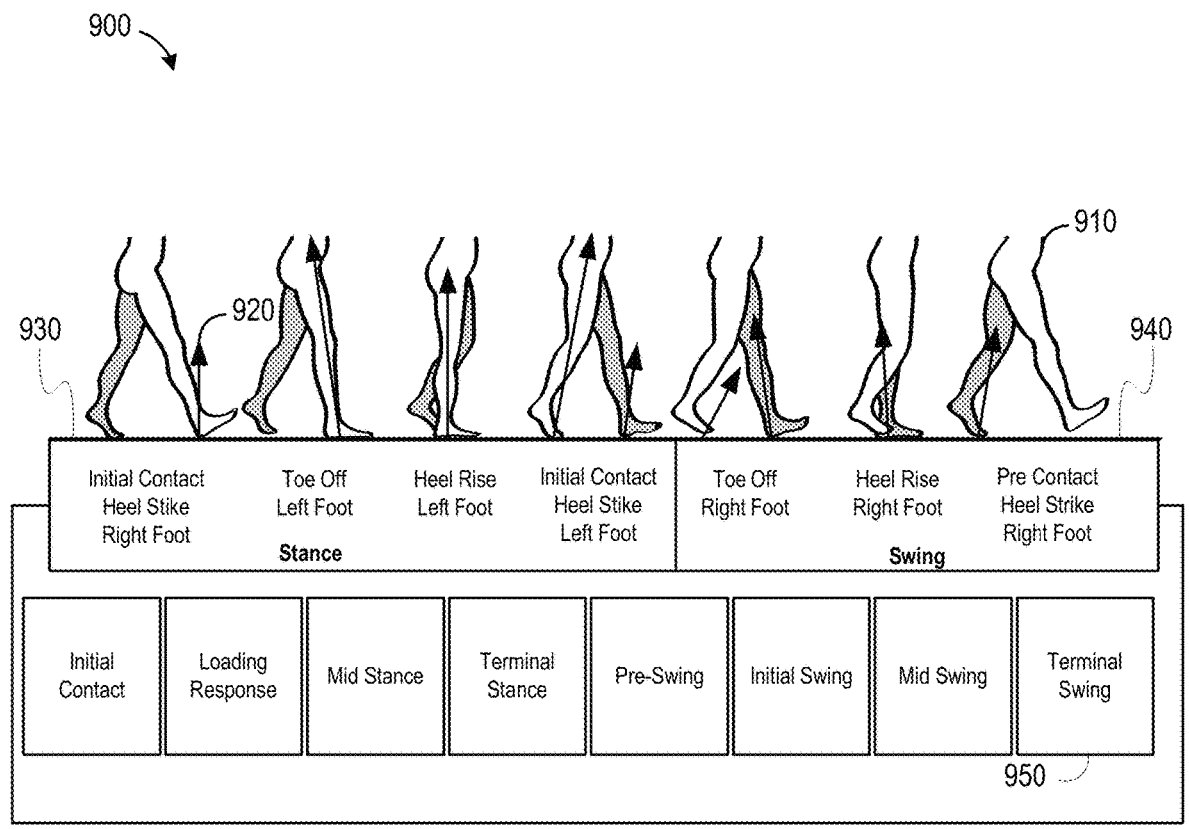
FIG. 9 shows a schematic diagram of an example of the different positions of the legs during a single gait cycle by the right leg.

Referring now to FIG. 9, shown therein is a schematic diagram of an example of the different positions 900 of the legs during a single gait cycle 910 by the right leg. The different positions 900 are also known as major events during the gait cycle, each of which leads into a period 950. Force vectors 920 on contact are illustrated for each major event.

The different positions 900 can be divided into two phases: stance 930 and swing 940. The stance 930 begins at an initial contact, which is a heel strike of the right foot. The swing 940 ends with pre-contact during an opposite toe push, which comes just before the heel strike of the right foot.

The different positions 900 subdivide the gait cycle into periods 950. The group 950 of periods starts with initial contact and ends with a terminal swing.

In the stance 930 phase, an initial contact leads to a loading response period. An opposite toe off leads to a mid-stance period. A heel rise leads to a terminal stance period. An opposite initial contact leads to a pre-swing period.

In the swing 940 phase, a toe off leads to an initial swing period. A heel rise leads to a mid-swing period. An opposite tow push leads to a terminal swing period.

Figure 10:
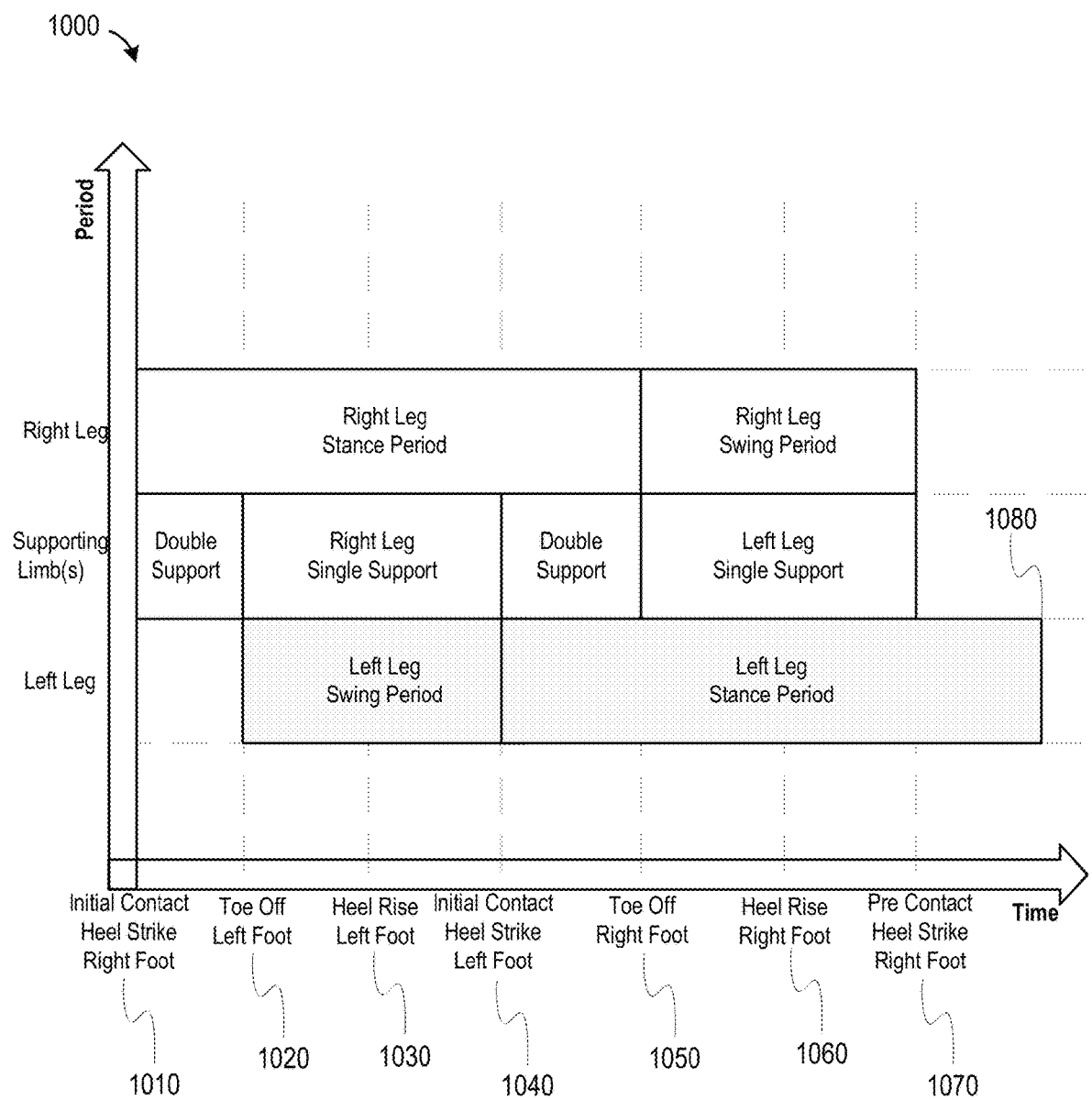
FIG. 10 shows a schematic diagram of an example of gait cycle timing, showing single and double support.

Referring now to FIG. 10, shown therein is a schematic diagram of an example of gait cycle timing 1000, showing single and double support.

At 1010, the right leg makes initial contact, and the left leg provides double support. The right stance phase begins.

At 1020, the left toe off begins the left swing phase, which initiates right single support.

At 1030, the left heel rise continues the left swing phase.

At 1040, the left initial contact ends the left swing phase, which provides double support.

At 1050, the right toe off begins the right swing phase, which initiates left single support.

At 1060, the right heel rise continues the right swing phase.

At 1070, the right initial contact ends the right swing phase, which provides double support.

At 1080, the left toe off ends the left stance phase.

Figure 11:
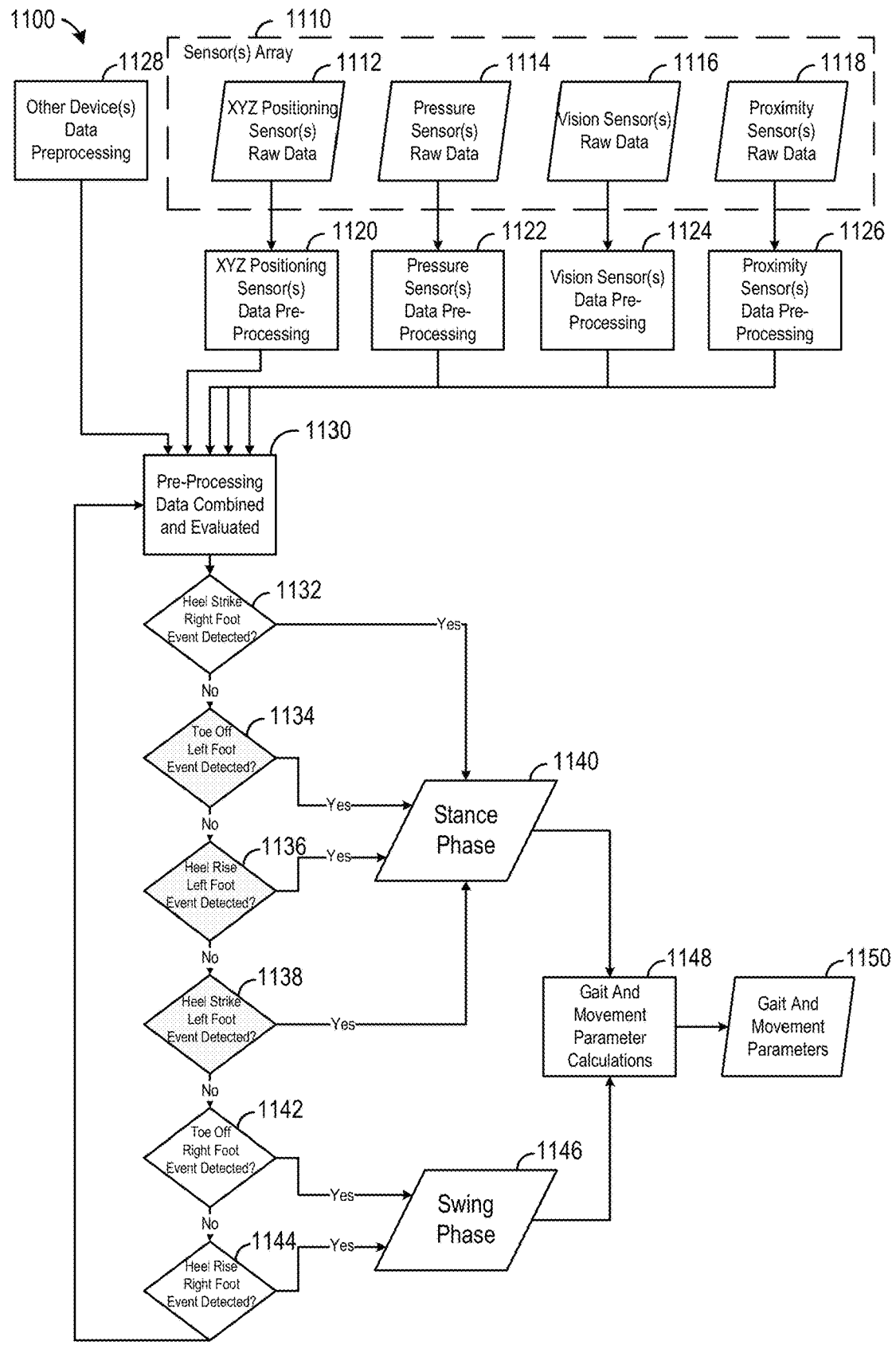
FIG. 11 shows a flow chart of an example embodiment of a method of gait parameter calculation.

Referring now to FIG. 11, shown therein is a flow chart of an example embodiment of a method 1100 of gait parameter calculation. The method 1100 uses a combination of various sensors to derive the gait cycle position and temporal/spatial parameters. The method 1100 can be executed by system 100. In other embodiments, different components (e.g., electrical, mechanical) may execute different parts of method 1100.

At 1110, the system 100 obtains raw data 360 from a sensor array 310. In particular, the system 100 may obtain one or more different types of raw data, each type of raw data generated by one or more sensors.

At 1112, the system 100 obtains XYZ positioning sensor(s) raw data.

At 1120, the system 100 performs data preprocessing on the XYZ positioning sensor raw data.

At 1114, the system 100 obtains pressure sensor(s) raw data.

At 1122, the system 100 performs data preprocessing on the pressure sensor(s) raw data.

At 1116, the system 100 obtains vision sensor(s) raw data.

At 1124, the system 100 performs data preprocessing on the vision sensor(s) raw data.

At 1118, the system 100 obtains proximity sensor(s) raw data.

At 1126, the system 100 performs data preprocessing on the proximity sensor(s) raw data.

At 1128, the system 100 performs data preprocessing of one or more of the other devices.

At 1130, the system 100 combines the results of the preprocessed data and evaluates the combined data.

At 1132, the system 100 determines whether a heel strike right foot event is detected. If Yes (i.e., a heel strike right foot event is detected), then the method 1100 proceeds to 1140. If No (i.e., a heel strike right foot event is not detected), then the method 1100 proceeds to 1134.

At 1134, the system 100 determines whether a toe off left foot event is detected. If Yes (i.e., a toe off left foot event is detected), then the method 1100 proceeds to 1140. If No (i.e., a toe off left foot event is not detected), then the method 1100 proceeds to 1136.

At 1136, the system 100 determines whether a heel rise left foot event is detected. If Yes (i.e., a heel rise left foot event is detected), then the method 1100 proceeds to 1140. If No (i.e., a heel rise left foot event is not detected), then the method 1100 proceeds to 1138.

At 1138, the system 100 determines whether a heel strike left foot event is detected. If Yes (i.e., a heel strike left foot event is detected), then the method 1100 proceeds to 1140. If No (i.e., a heel strike left foot event is not detected), then the method 1100 returns to 1142.

At 1140, the system 100 acquires data on the stance phase, such as when the stance phase started.

At 1146, the system 100 acquires data on the swing phase, such as when the swing phase started.

At 1148, the system 100 calculates gait and movement parameters based on at least one of the detection results and optionally other device data. The detection results may be generated, for example, from data acquired during the stance phase 1140 or the swing phase 1146.

At 1150, the system 100 outputs the gait temporal and spatial parameters.

In at least one embodiment, the method 1100 is stored as a plurality of instructions on a non-transitory computer-readable medium that is executable by a processor of a system for adapting the system to implement the method 1100. The system may be system 100, where, for example, the non-transitory computer-readable medium is data store 120 and the processor is microcontroller 115.

Figure 12A:
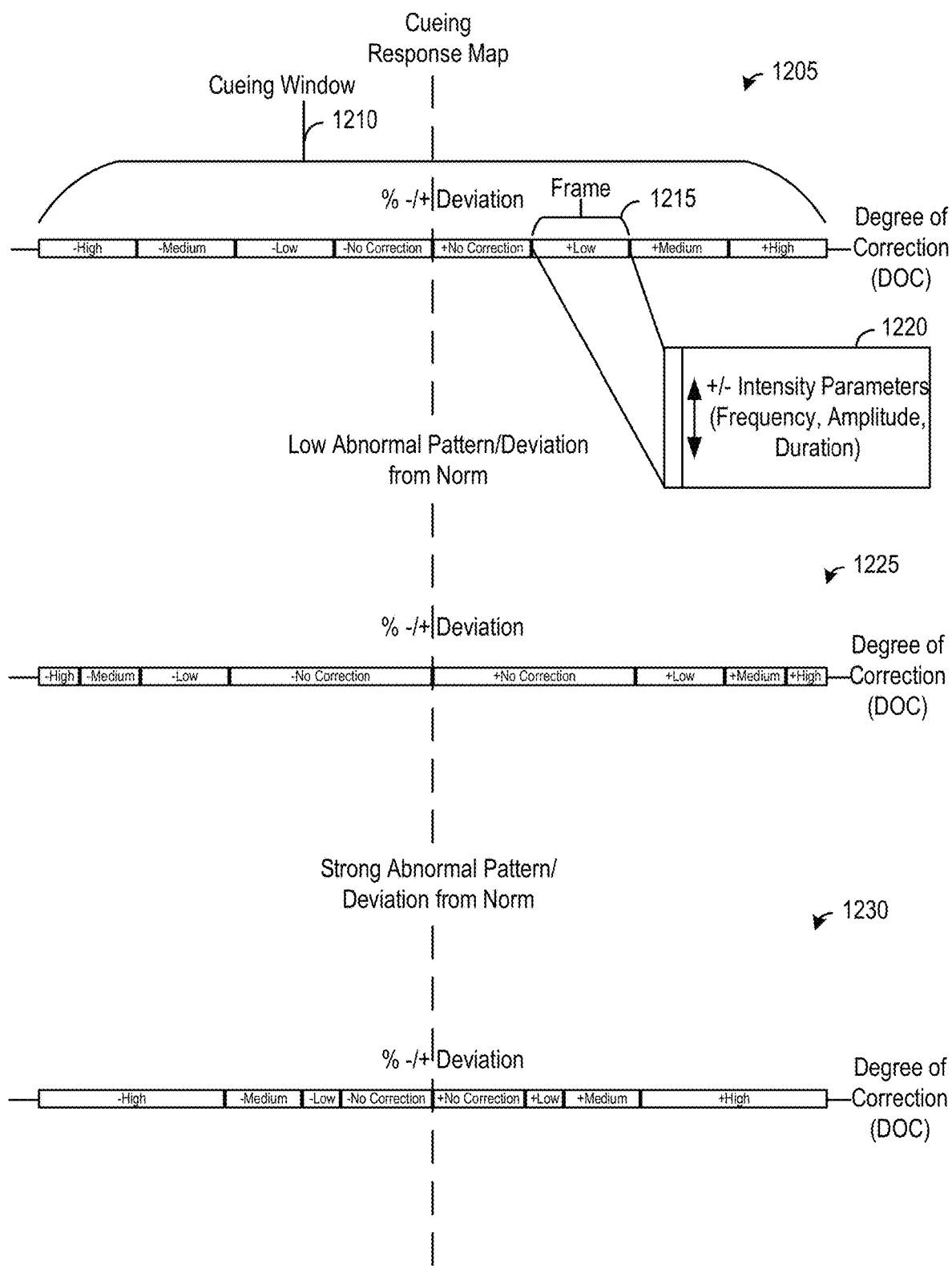
FIG. 12A shows a schematic diagram of an example embodiment of a cueing response map for use with a method of cueing intensity calculation.

Referring now to FIG. 12A, shown therein is a schematic diagram of an example embodiment of a cueing response map 1205 for use with a method 1200 of cueing intensity (or degree of correction) calculation. The cueing response map 1205 may be used for dynamic tuning, such as providing the appropriate amount of correction, in the form of a cueing response, for a particular level of deviation or abnormal pattern in the patient's gait. The cueing response may become dialed in through machine learning.

The cueing response map 1205 comprises a cueing window 1210. The cueing window comprises a plurality of frames 1215 that may correspond to a percentage (or some other suitable measure, such as number of degrees) deviation or abnormal pattern (e.g., relating to timing). The plurality of frames 1215 may be categorized by degree of correction (DOC) as no correction, low correction, medium correction, and high correction. Each frame 1215 comprises intensity parameters 1220 such as frequency, amplitude, and duration for cueing. The method 1200 may, for example, use the cueing response map 1205 as input for determining how much to increase/decrease the amount of cueing response based on the percentage increase/decrease in deviation.

For example, suppose the system 100 is used to correct in-toeing. A value 'D' may be used to denote the number of degrees of deviation, and |D| may be used to denote the absolute value of 'D'. A first cueing response map 1225 may be configured for a first set of values of 'D' for a first degree of correction as follows:

$0<=|D|<5°$, no correction.
$5°<=|D|<10°$, low correction (or low intensity cueing)
$10°<=|D|<15°$, medium correction (or medium intensity cueing)
$15°<=|D|$, high correction (or high intensity cueing).

For ease of reference, the first set of values, such as 5°, 10°, and 15°, may be referred to as a first low intensity deviation, a first medium intensity deviation, and a first high intensity deviation, respectively.

Now suppose the system 100 is adjusted (e.g., by a clinician or as a result of machine learning), a second cueing response map 1230 may be configured for a second set of values of '|D|' for a second degree of correction as follows:

$0<=|D|<2°$, no correction.
$2°<=|D|<5°$, low correction (or low intensity cueing)
$5°<=|D|<7°$, medium correction (or medium intensity cueing)
$7°<=|D|$, high correction (or high intensity cueing).

For ease of reference, the second set of values, such as 2°, 5°, and 7°, may be referred to as a second low intensity deviation, a second medium intensity deviation, and a second high intensity deviation, respectively.

The system 100 may have more or fewer values within each set of values of 'D'. For example, there may be only one value or two values, instead of three (like in first cueing response map 1225 or second cueing response map 1230). For example, there may be four of more values. Alternatively, or in addition, there may be a continuous range of values (as opposed to discrete values) for such that the intensity of cueing may be calculated as a function of 'D'.

Figure 12B:
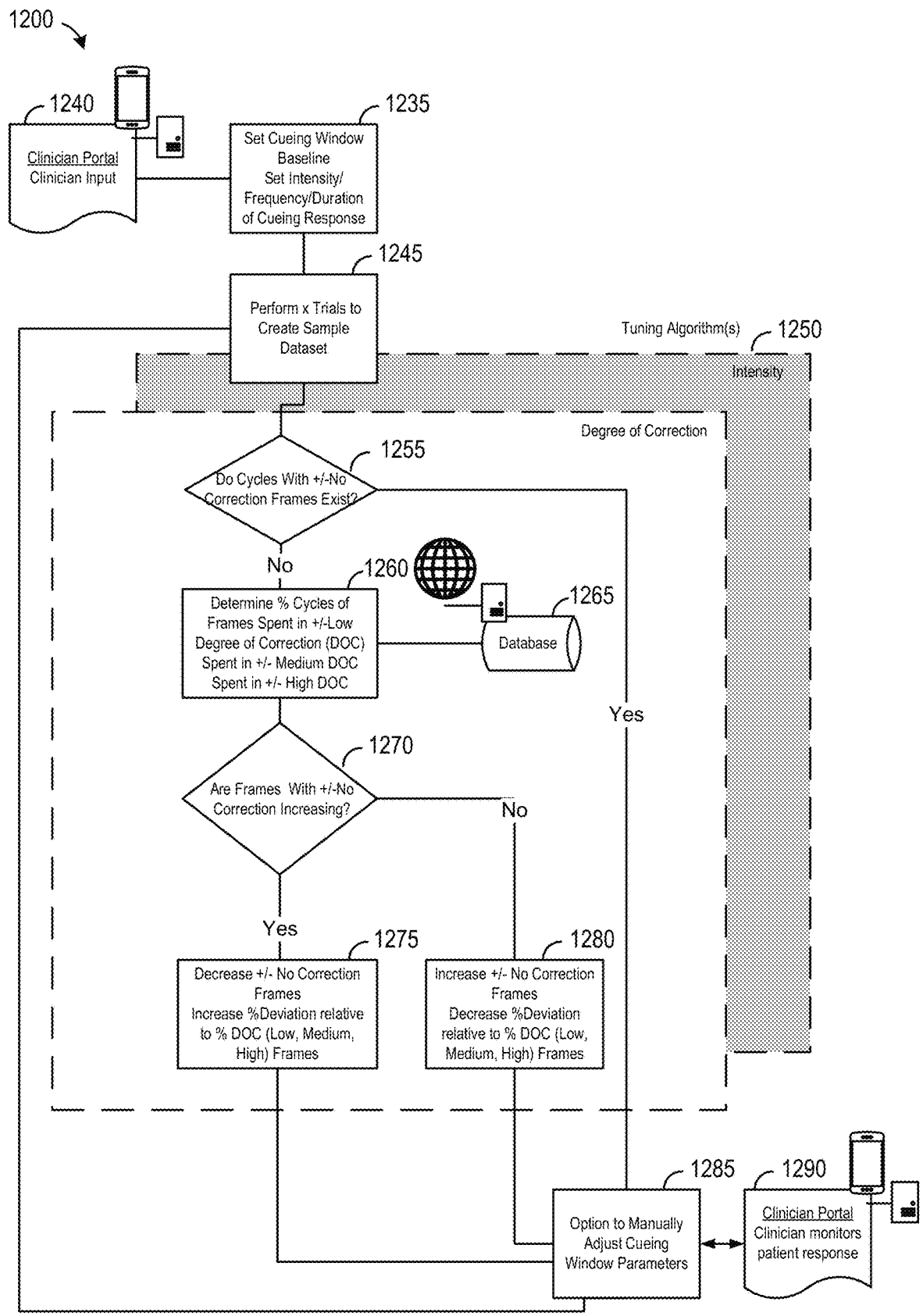
FIG. 12B shows a flow chart of an example embodiment of a method of cueing intensity calculation.

Referring now to FIG. 12B, shown therein is a flow chart of an example embodiment of a method 1200 of cueing intensity (or degree of correction) calculation. Method 1200 may be carried out, for example, by system 100.

At 1235, the system 100 selects initial ranges for one or more cueing response variables for a baseline cueing window 1210, which may be based at least in part on data received from a clinician portal. The cueing response variables may be, for example, intensity, frequency, or duration. The initial ranges may be divided, for example, into a low range, a medium range, and a high range.

At 1240, the system 100 receives clinical data from a clinician portal, which may include clinician input such as kinematic data and a clinical assessment file. The clinician portal may be, for example, the clinician portal 220 on cloud network 200.

At 1245, the system 100 performs a certain number of (e.g., consecutive) trials to create a sample dataset. The dataset may be stored in database 147. Alternatively, or in addition, the system 100 may receive the sample dataset from the wearable device 110.

At 1250, the system 100 optionally enters into cueing intensity calculation, which may be performed before, during, or after degree of correction (DOC) calculation.

At 1255, the system 100 determines whether cycles with "no correction" frames exist. If Yes (i.e., "no correction" frames exist), then the method 1200 proceeds to 1285. If No (i.e., "no correction" frames do not exist), then the method 1200 proceeds to 1260.

At 1260, the system 100 determines the percentage (or proportion) of cycles of frames spent in a low DOC frame, a medium DOC frame, and a high DOC frame.

At 1265, the system 100 stores the data received from 1260 into the database 147.

At 1270, the system 100 determines whether frames with "no correction" are increasing. If Yes (i.e., frames with "no correction" are increasing), then the method 1200 proceeds to 1275. If No (i.e., frames with "no correction" are not increasing), then the method 1200 proceeds to 1280.

At 1275, the system 100 decreases the "no correction" frames and increases the percentage deviation relative to the DOC (e.g., low, medium, and high) frames.

At 1280, the system 100 increases the "no correction" frames and decreases the percentage deviation relative to the DOC (e.g., low, medium, and high) frames.

At 1285, the system 100 provides a recommendation (e.g., to the clinician) to adjust the values of the cueing window 1210, such as the cueing response variables, the parameters 1220, or the degree of correction (e.g., to a higher or lower order of magnitude). Alternatively, or in addition, the system 100 can automatically adjust the range to a different (e.g., higher or lower) order of magnitude (e.g., based on the system 100 learning the patient's progress).

At 1290, the system 100 generates a report to send to the clinician portal. The report may be based on the nature and timing of the adjustments. The report may include data or analytics. Alternatively, or in addition, the report may be sent to the database 147.

In at least one embodiment, the method 1200 is iterative, returning, for example to 1245 or 1255, whenever the cueing response is set to a range of bounds at a different order of magnitude.

In at least one embodiment, the system 100 performs hypothesis testing based on the data generated from the patient's performance and responses.

In at least one embodiment, the method 1200, after consecutive trials, based on data from database 147 and kinetic data from the device, selects a next level of intensity for frequency, amplitude, and duration within a range. If the highest value within a range is met without result, the system 100 provides a suggestion on the clinician portal to move the range to a next level. The opposite is done if lower bounds are being met too easily. Essentially, the scale shifts to challenge the patient to eventually meet a response within the normal parameters established by the database 147.

In at least one embodiment, the method 1200 is stored as a plurality of instructions on a non-transitory computer-readable medium that is executable by a processor of a system for adapting the system to implement the method 1200. The system may be system 100, where, for example, the non-transitory computer-readable medium is data store 120 and the processor is microcontroller 115.

Figure 13:
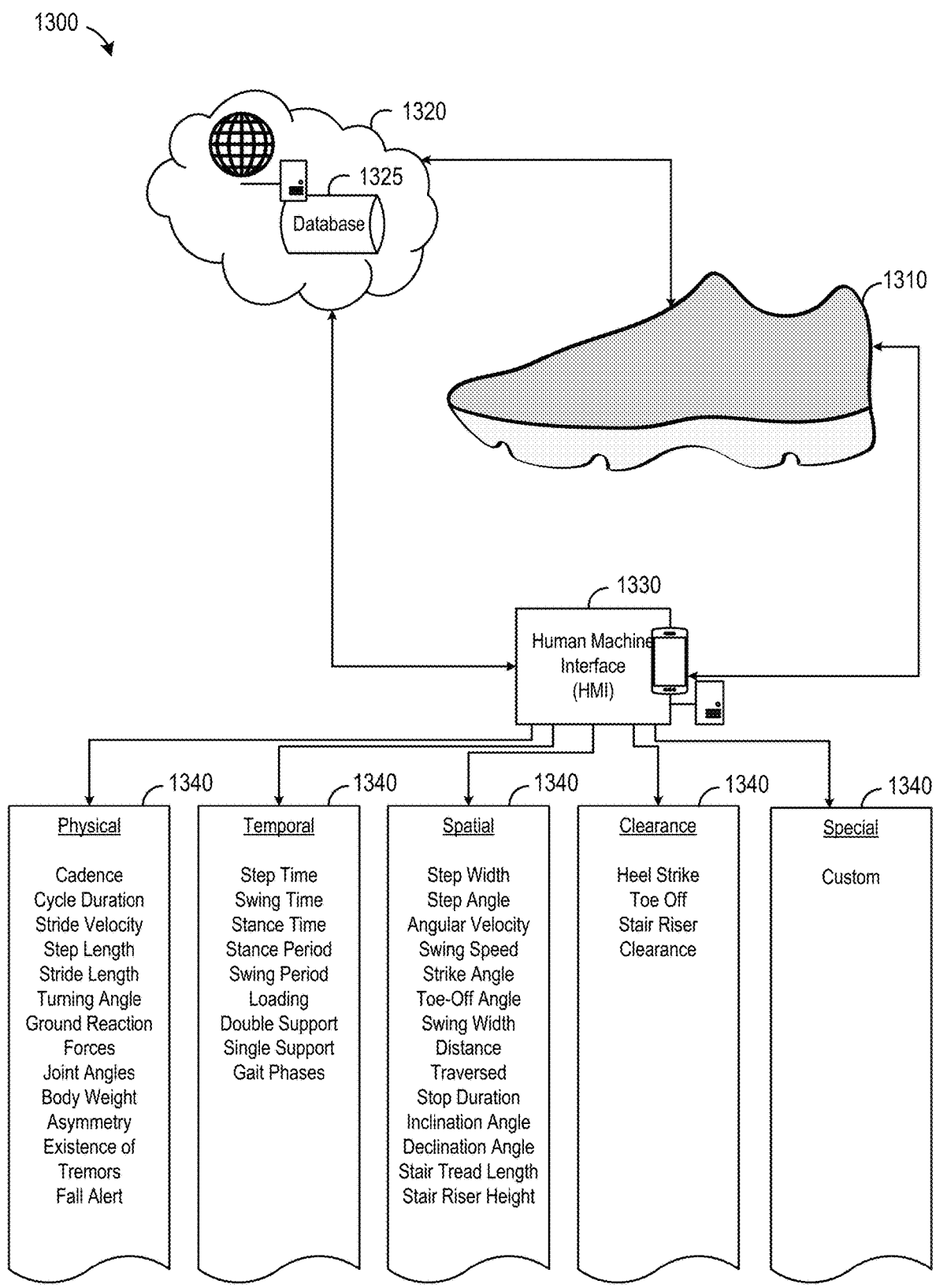
FIG. 13 shows a block diagram of an example embodiment of a system for obtaining measurable gait parameters of interest.

Referring now to FIG. 13, shown therein is a block diagram of an example embodiment of a system 1300 for obtaining measurable gait parameters of interest.

System 1300 comprises a wearable device 1310 connected to the cloud 1320 and a human machine interface (HMI) 1330. The cloud 1320 comprises a database 1325. The database 1325 may be, for example, database 147. The HMI 1330 may receive, store, generate, and or display one or more measurable gait parameters 1340. The measurable gait parameters 1340 may be classified into categories such as physical, temporal, spatial, clearance, and special.

Physical parameters may include, for example, cadence, cycle duration, stride velocity, step length, stride length, turning angle, ground reaction, forces, joint angles, body weight, asymmetry, existence of tremors, or fall alert.

Temporal parameters may include, for example, step time, swing time, stance time, stance period, swing period, loading, double support, single support, or gait phases.

Spatial parameters may include, for example, step width, step angle, angular velocity, swing speed, strike angle, toe-off angle, swing width, distance traversed, stop duration, inclination angle, declination angle, stair tread length, or stair riser height.

Clearance parameters may include, for example, heel strike, toe off, stair riser, or clearance.

Special parameters may include, for example, parameters that are custom-made, which may or may not be related to locomotion, such as executing dance moves, tumbling, kicking, tripping, transitioning to sitting, transitioning to standing, or jumping, to name a few.

Figure 14:
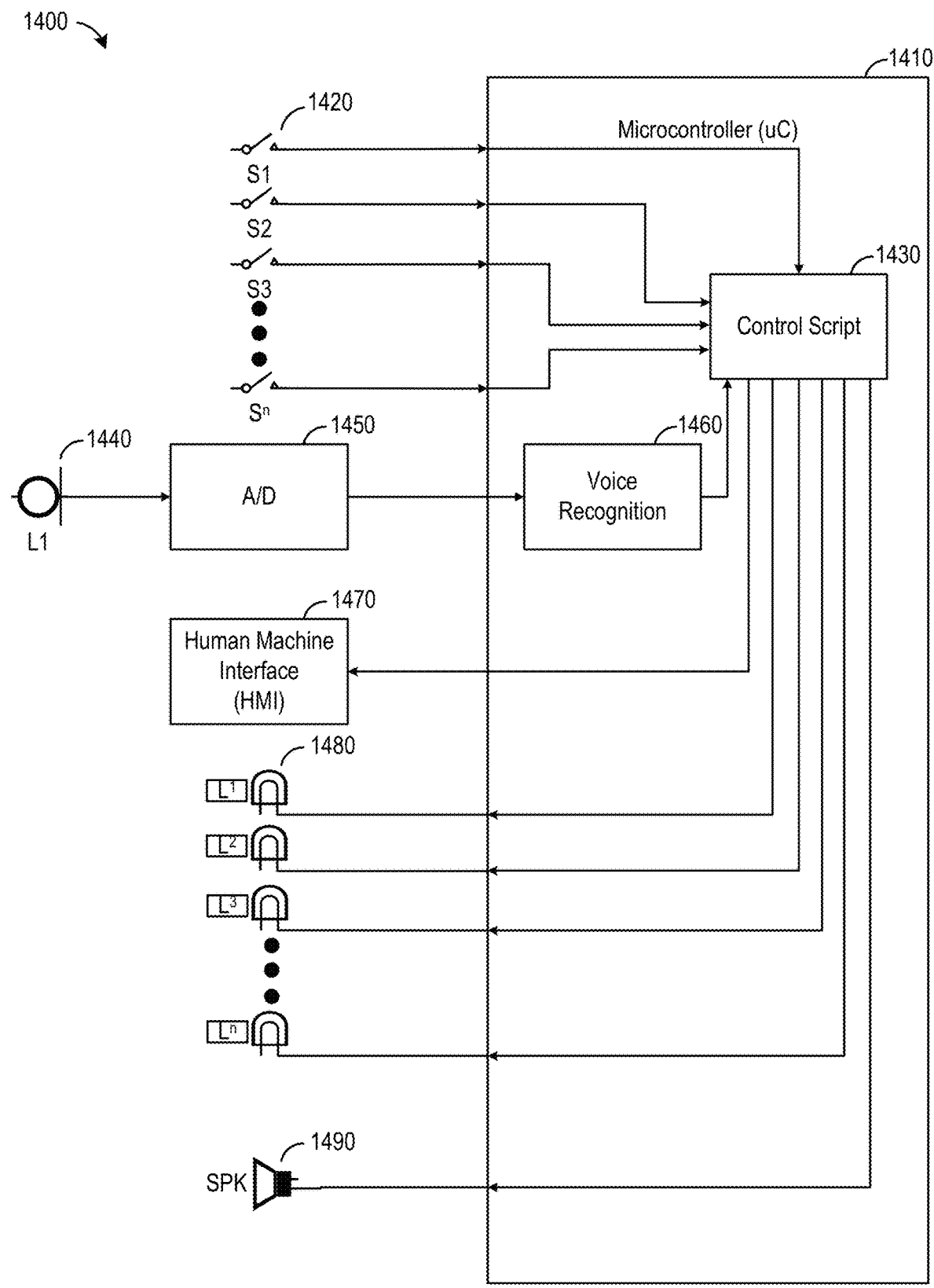
FIG. 14 shows a schematic diagram of an example embodiment of a manual control for a system for gait monitoring and improvement.

Referring now to FIG. 14, shown therein is a schematic diagram of an example embodiment of a manual control 1400 for system 100.

The manual control 1400 comprises a microcontroller 1410 to receive inputs, process the inputs, and generate outputs. The inputs may include signals from switches 1420 and sound files from an analog-to-digital (A/D) converter 1450. The components that process the inputs may include a control script 1430 and a voice recognition module 1460. The outputs may include data to a human machine interface (HMI) 1470, signals to light-emitting diodes (LEDs) 1480, and signals to a speaker 1490.

The manual control 1400 comprises a microphone 1440 that receives audio input. The audio input is processed by the A/D converter 1450, generating a digital sound file. The digital sound file is processed by the voice recognition module 1460. The output of the voice recognition module 1460 is sent to the control script module 1430.

The control script module 1430 may receive signals from the switches 1420 and data from the voice recognition module 1460. The control script module 1430 may execute scripts to process the signals and data received by it. The control script module 1430 may generate outputs based on the signals and data, then send these outputs to the HMI 1470, the LEDs 1480, and/or the speaker 1490.

Figure 15:
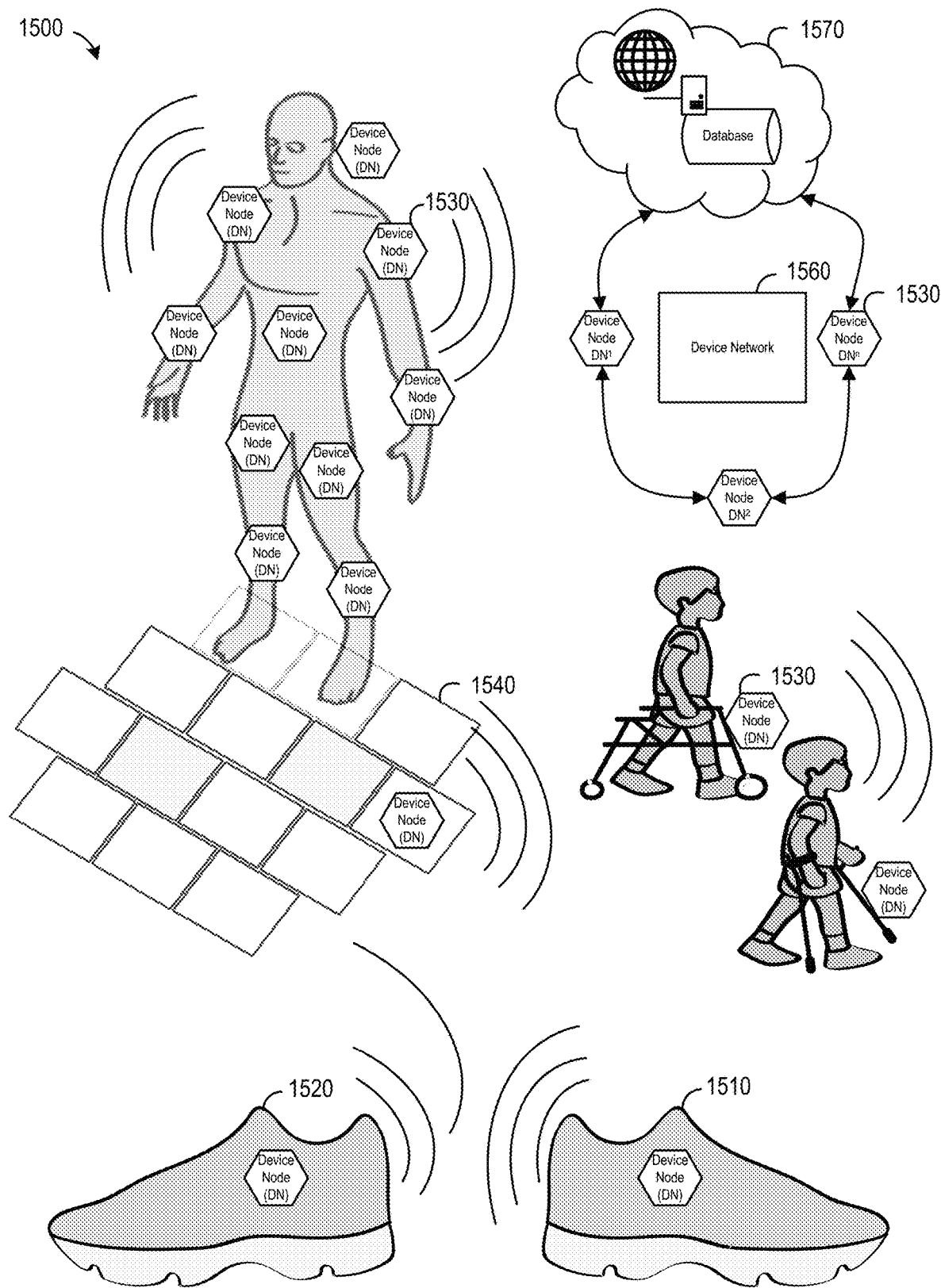
FIG. 15 shows a schematic diagram of an example embodiment of networking setup between devices.

Referring now to FIG. 15, shown therein is a schematic diagram of an example embodiment of a networking setup 1500 between devices. One or more of the devices may be a wearable device or other device of system 100.

The networking setup 1500 provides a communications link between device nodes 1530, a device network 1560, and/or the cloud 1570. The device nodes 1530 may be wearable devices, or they may be integrated into the wearable devices, such as the right wearable device 1510 and the left wearable device 1520 (which together may be a pair of shoes or sole attachments). The device nodes 1530 may also be placed on the body at various positions on or near the human body. The device nodes 1530 may also be placed on or integrated into assistive devices. The networking setup 1500 may provide networking capabilities with other sensors, thus providing expandability, placed on the body. The networking setup 1500 may provide a communications link between the components of the system on the shoes, sensor cueing modules, and other body parts.

The networking setup 1500 may provide a communications link for data transfer between each of the device nodes 1530 on the device network 1560. The device nodes 1530 may interact with an outside device 1540, such as a flooring tile configured as a game, or a zone that must be avoided. The individual device nodes 1530 may communicate with the cloud 1570. Alternatively, or in addition, the device network 1560 may provide centralized communication with the cloud 1570. The cloud 1570 may range in size and complexity from a single host to the Internet.

Figure 16:
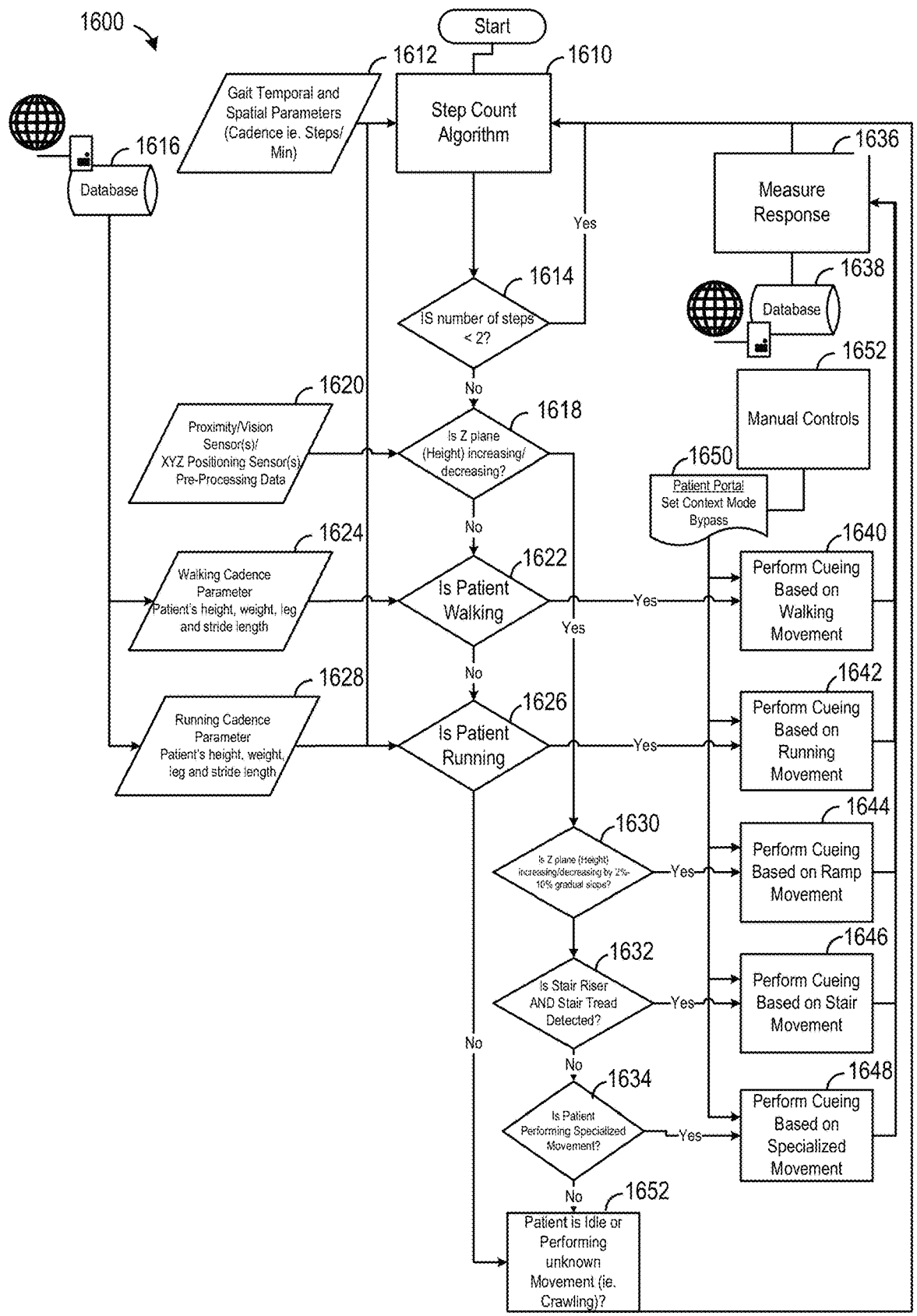
FIG. 16 shows a flow chart of an example embodiment of a method of performing cueing during gait monitoring and improvement.

Referring now to FIG. 16, shown therein is a flow chart of an example embodiment of a method 1600 of performing cueing during gait monitoring and improvement. Method 1600 may be carried out, for example, by system 100. The method 1600 may determine an activity type (or a "context"), which may include, for example, walking, running, ambulating with a mobility aid (e.g., cane, crutch, walker), going up/down an incline (e.g., ramp), ascending/descending stairs, idling (e.g., no movement), performing a custom movement, performing a specialized movement, and performing an unknown movement. The activity type may also include transitioning from one activity type to another activity type. The activity type may be divided into categories, such as (a) movement without vertical changes and (b) movement with vertical changes.

At 1610, the system 100 initiates a step count program. The step count program may take as input data from a database, the caregiver portal, the clinician portal, the wearable device, and/or the cloud. The step count program may track the number of steps taken by a patient, the timing of the steps, the distance between steps, the coordinates of the steps, or derived quantities such a speed.

At 1612, the system 100 receives gait temporal and spatial parameters (such as cadence in steps per minute). These parameters may be used as input in the step count program at 1610.

At 1614, the system 100 determines whether the number of steps is less than two. If Yes (i.e., the number of steps is less than two), then the method 1600 returns to 1610. If No (i.e., the number of steps is not less than two), then the method 1600 proceeds to 1618.

At 1616, the database provides activity type related (or "context-related") data to the system 100. The data may include, for example, walking cadence parameters, running cadence parameters, and patient characteristics (e.g., height, weight, leg length, stride length). The data may include activity properties where, for example, the existence of a certain set of activity properties may indicate the presence of a particular activity type.

At 1618, the system 100 determines whether the Z plane (e.g., mean height) is increasing or decreasing. The system 100 may evaluate the extent of the changes in mean height, for example, in terms of absolute changes, relative changes, or changes over time. If Yes (i.e., the Z plane is increasing or decreasing), then the method 1600 proceeds to 1630. If No (i.e., the Z plane is not increasing or decreasing), then the method 1600 proceeds to 1622. The system 100 may make this determination based at least in part on proximity/vision sensor(s) or XYZ positioning sensor(s) pre-processing data.

At 1620, the system 100 receives (or generates) proximity/vision sensor(s) or XYZ positioning sensor(s) pre-processing data.

At 1622, the system 100 determines whether the patient is walking. If Yes (i.e., the patient is walking), then the method 1600 goes to 1640. If No (i.e., the patient is not walking), then the method 1600 proceeds to 1626. The system 100 may make this determination based at least in part on walking cadence parameters and/or patient characteristics (e.g., height, weight, leg length, stride length).

At 1624, the system 100 receives (or generates) walking cadence parameters and/or patient characteristics (e.g., height, weight, leg length, stride length).

At 1626, the system 100 determines whether the patient is running. If Yes (i.e., the patient is running), then the method 1600 goes to 1642. If No (i.e., the patient is not running), then the method 1600 proceeds to 1652. The system 100 may make this determination based at least in part on running cadence parameters and/or patient characteristics (e.g., height, weight, leg length, stride length).

At 1628, the system 100 receives (or generates) running cadence parameters and/or patient characteristics (e.g., height, weight, leg length, stride length).

At 1630, the system 100 determines whether the Z plane (i.e., height) is increasing or decreasing by a gradual (e.g., 2% to 10%) slope. If Yes (i.e., the Z plane is increasing or decreasing by a gradual slope), then the method 1600 goes to 1644. If No (i.e., the Z plane is not increasing or decreasing by a gradual slope), then the method 1600 proceeds to 1632.

At 1632, the system 100 determines whether both a stair riser and a stair tread are detected. If Yes (i.e., both a stair riser and a stair tread are detected), then the method 1600 goes to 1646. If No (i.e., either a stair riser or a stair tread is not detected), then the method 1600 proceeds to 1634.

At 1634, the system 100 determines whether the patient is performing a specialized movement (e.g., sidestepping). If Yes (i.e., the patient is performing a specialized movement), then the method 1600 goes to 1648. If No (i.e., the patient is not performing a specialized movement), then the method 1600 proceeds to 1652.

At 1636, the system 100 measures the patient's response. The measurement may be obtained from one or more sensors on the wearable device.

At 1638, the system 100 sends the measurements to the database.

At 1640, the system 100 performs cueing based on walking movement.

At 1642, the system 100 performs cueing based on running movement.

At 1644, the system 100 performs cueing based on ramp movement.

At 1646, the system 100 performs cueing based on stair movement.

At 1648, the system 100 performs cueing based on specialized movement.

At 1650, the system 100 receives a command from the patient portal to set activity type (or "context") mode bypass. The bypass may be entered, for example, to continue performing cueing based on one type of movement even though the patient's movement varies.

At 1652, the system 100 records that the patient is idle or performing an unknown movement (e.g., crawling). The method 1600 may return to 1610.

In at least one embodiment, the method 1600 combines one or more decision blocks, such as 1618, 1622, 1626, 1630, 1632, and 1634, into one decision block. For example, decision blocks 1622 and 1626 can be combined into one decision block corresponding to movement with no change in mean height (or altitude), while decision blocks 1630, 1632, and 1634 can be combined into one decision block corresponding to movement involving a change in mean height (or altitude).

In at least one embodiment, the method 1600 includes the system 100 receiving additional or alternative inputs (e.g., changing cueing manually, updating input data, pausing the method, restarting the method, halting the method).

In at least one embodiment, the method 1600 includes the system 100 providing additional or alternative outputs (e.g., based on new inputs).

Figure 17:
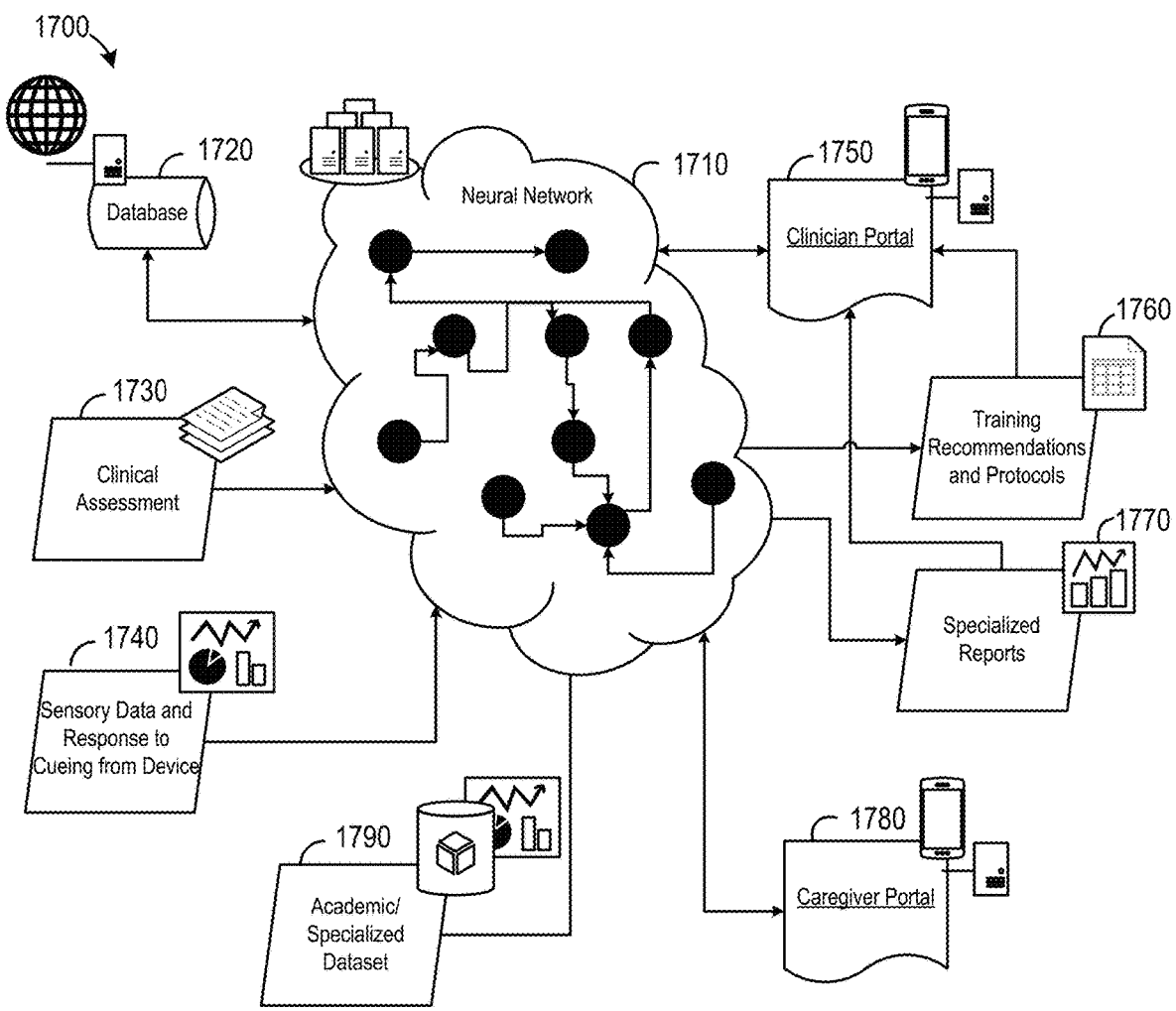
FIG. 17 shows a block diagram of an example embodiment of a topology for neural network inputs and outputs for use with a system for gait monitoring and improvement.

Referring now to FIG. 17, shown therein is a block diagram of an example embodiment of a topology 1700 for neural network inputs and outputs for use with a system for gait monitoring and improvement. The topology 1700 may be used, for example, by system 100.

The topology includes a neural network 1710 and various devices, files, or data that serve as inputs or outputs (or both). The neural network 1710 may be, for example, a convolutional neural network (e.g., for classification prediction), a recurrent neural network (e.g., for sequence prediction), or other artificial neural network. In other embodiments, the neural network 1710 may be replaced by another form of machine learning, such as a support-vector machine (SVM), Bayesian network, or random forest classifier.

The inputs may come from a database 1720, a clinical assessment file 1730, sensory data and responses to cueing 1740 from the wearable device, a clinician portal 1750, and a caregiver portal 1780.

The outputs may go to the database 1720, the clinician portal 1750, a training recommendations and protocols file 1760, specialized reports 1770, the caregiver portal 1780, and an academic/specialized dataset 1790.

The clinician portal 1750 may receive the training recommendations and protocols file 1760 and the specialized reports 1770, which may, for example, be viewable on the clinician's computing device.

In at least one embodiment, the outputs of the neural network 1710 include dynamic adjustments such as real-time adjustments to range, as well as amplitude and frequency response of cueing devices.

Figure 18A:
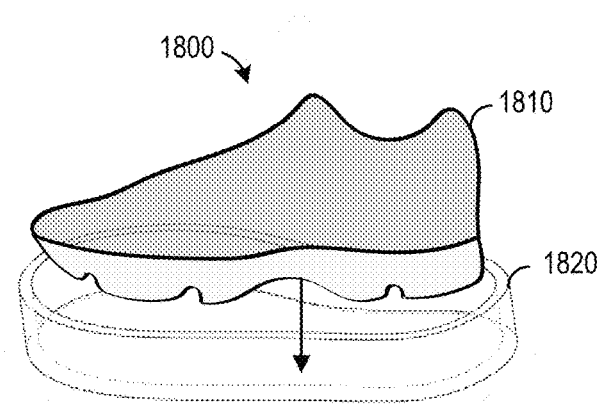
FIG. 18A shows an illustration of an example embodiment of a wearable device configuration using a sole attachment for use with a system for gait monitoring and improvement.

Referring now to FIG. 18A, shown therein is an illustration of an example embodiment of a wearable device configuration 1800 using a shoe attachment for use with a system for gait monitoring and improvement.

The wearable device configuration 1800 comprises a shoe 1810 (or other footwear) that can be inserted into a wearable device 1820. The wearable device 1820 may completely surround the bottom of the shoe 1810 using a friction fit. Alternatively, or in addition, the wearable device 1820 may be attached to the shoe 1810 using one or more different types of attachment mechanisms, such as a strap, hook and loop, an adhesive, magnets, slide locks, etc.

In at least one embodiment, the wearable device configuration 1800 comprises a wearable device 1820 that can be placed on the top of the shoe 1810. For example, the wearable device 1820 may be placed on or inserted into laces of the shoe 1810. As another example, the wearable device 1820 may be attached to a hook and loop fastener on the top of the shoe 1810.

Figure 18B:
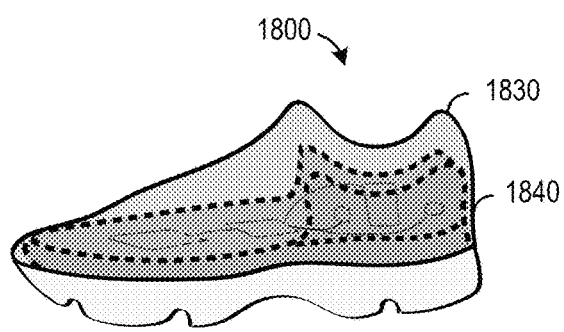
FIG. 18B shows an illustration of an example embodiment of a wearable device configuration using an insole or sock for use with a system for gait monitoring and improvement.

Referring now to FIG. 18B, shown therein is an illustration of an example embodiment of a wearable device configuration 1800 using an insole or sock for use with a system for gait monitoring and improvement. The wearable device configuration 1800 comprises a shoe 1830 (or other footwear) into which an insole or sock 1830 can be inserted.

Figure 18C:
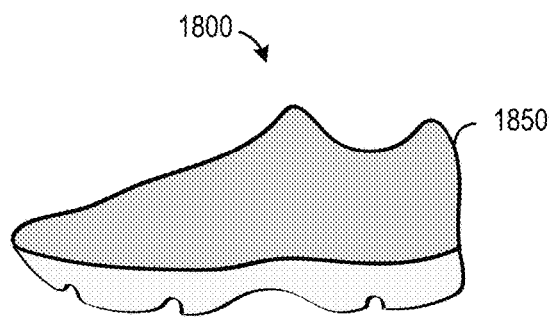
FIG. 18C shows an illustration of an example embodiment of a wearable device configuration using standalone footwear for use with a system for gait monitoring and improvement.

Referring now to FIG. 18C, shown therein is an illustration of an example embodiment of a wearable device configuration 1800 using standalone footwear for use with a system for gait monitoring and improvement. The wearable device configuration 1800 comprises a shoe 1850 (or other footwear) with one or more parts of the system for gait monitoring and improvement integrated therein.

Figure 18D:
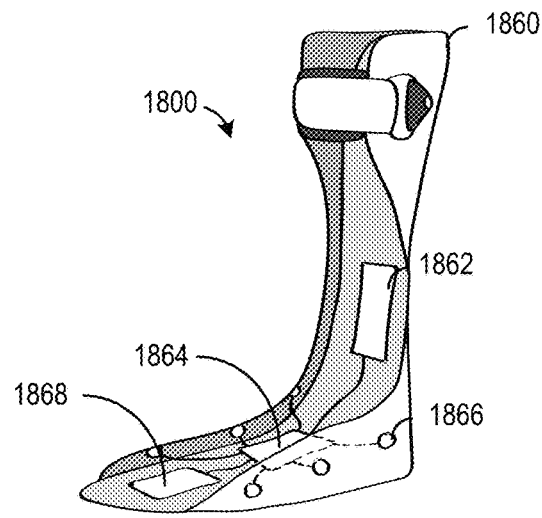
FIG. 18D shows an illustration of an example embodiment of a wearable device configuration using components built or incorporated into an orthotic for use with a system for gait monitoring and improvement.

Referring now to FIG. 18D, shown therein is an illustration of an example embodiment of a wearable device configuration 1800 using components built or incorporated into an orthotic for use with a system for gait monitoring and improvement. The wearable device configuration 1800 comprises a battery 1862, a microcontroller 1864, a sensor array 1866, and a cueing array 1868.

Figure 19:
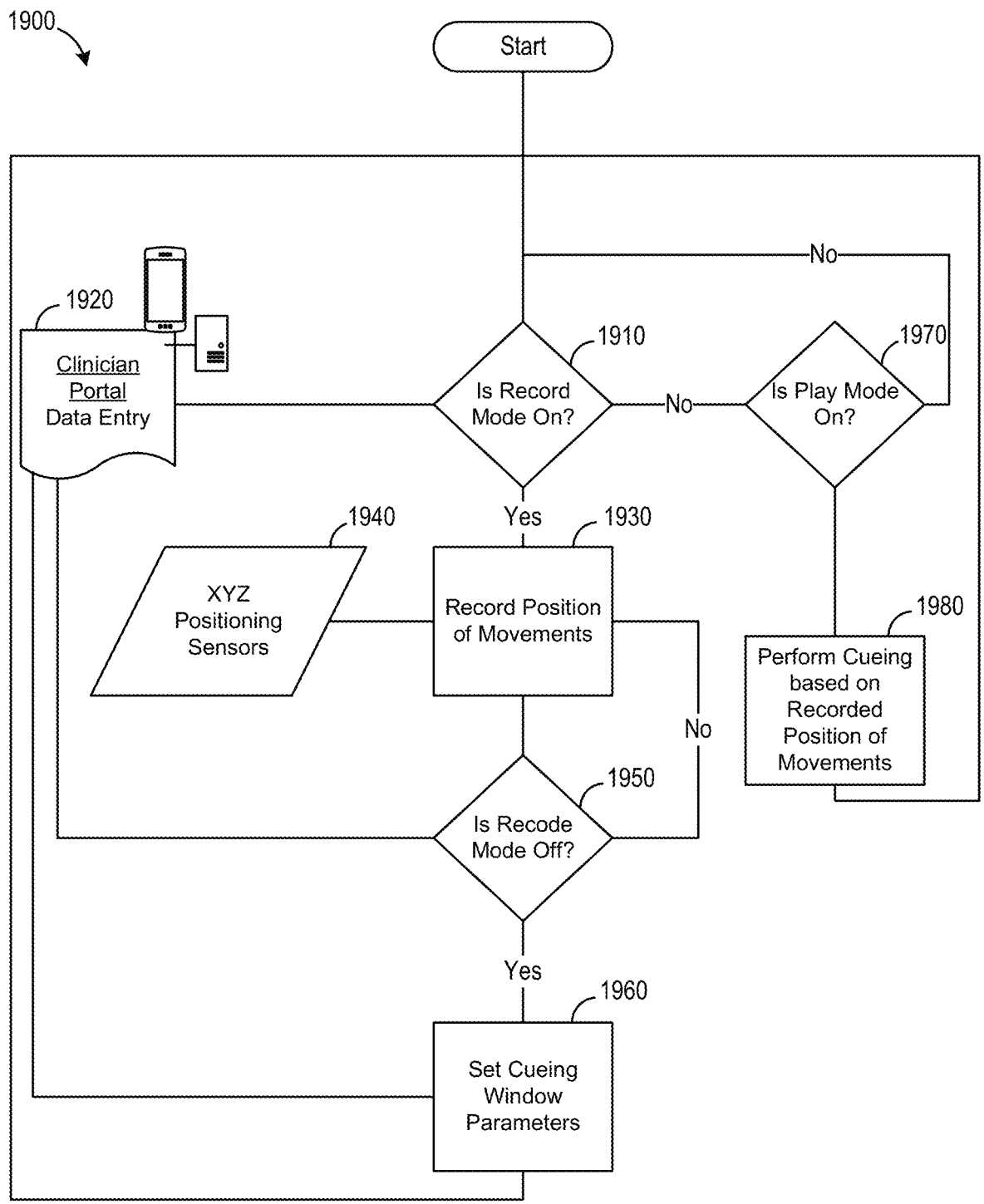
FIG. 19 shows a flow chart of an example embodiment of a method for recording and playing for use with a system for gait monitoring and improvement.

Referring now to FIG. 19, shown therein is a flow chart of an example embodiment of a method 1900 for recording and playing for use with a system for gait monitoring and improvement. Method 1900 may be carried out, for example, by system 100.

At 1910, the system 100 determines whether recording mode is on. If Yes (i.e., recording mode is on), then the method 1900 proceeds to 1930. If No (i.e., recording mode is not on), then the method proceeds to 1970.

At 1920, the system 100 receives data from the clinician portal 220.

At 1930, the system 100 records positions of movements. The positions of movements may be obtained from xyz positioning sensors such as MPU 322.

At 1940, the system 100 obtains position data (e.g., positions of movements) from the xyz positioning sensors.

At 1950, the system 100 determines whether recording mode is off. The determination may be made based on data obtained from the clinician portal 220. If Yes (i.e., recording mode is off), then the method 1900 proceeds to 1960. If No (i.e., recording mode is not off), then the method 1900 returns to 1930.

At 1960, the system 100 sets cueing window parameters. The setting of cueing window parameters may be based on data obtained from the clinician portal 220.

At 1970, the system 100 determines whether play mode is on. If Yes (i.e., play mode is on), then the method 1900 proceeds to 1980. If No (i.e., play mode is not on), then the method returns to 1910.

At 1980, the system 100 performs cueing based on the recorded positions of movements.

Figure 20A:
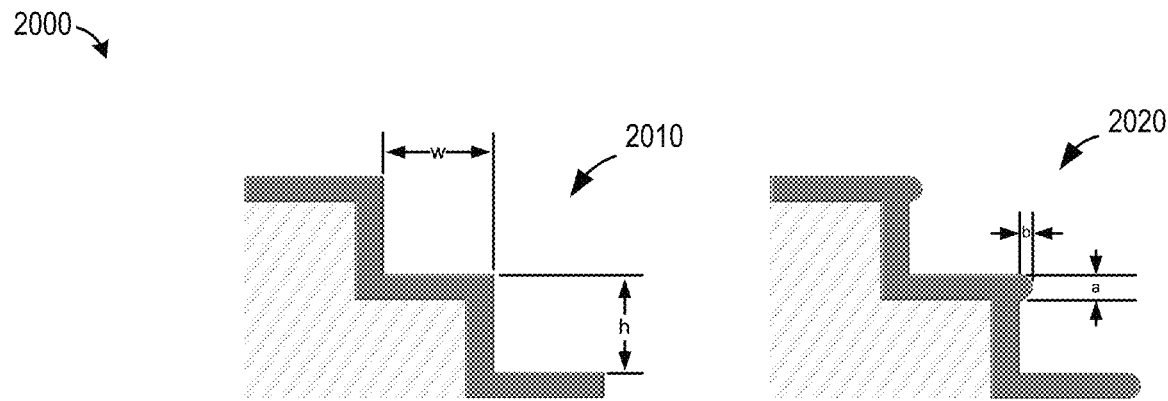
FIG. 20A shows an illustration of an example embodiment of stair guidance determining dimensions for stairs without and with nosing.
Figure 20B:
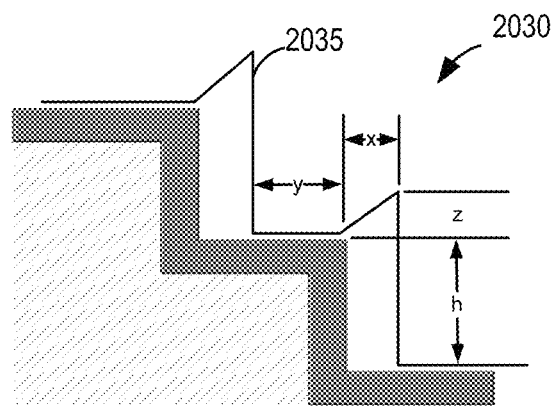
FIG. 20B shows an illustration of an example embodiment of stair guidance determining a clearance path around a stair nosing.
Figure 20C:
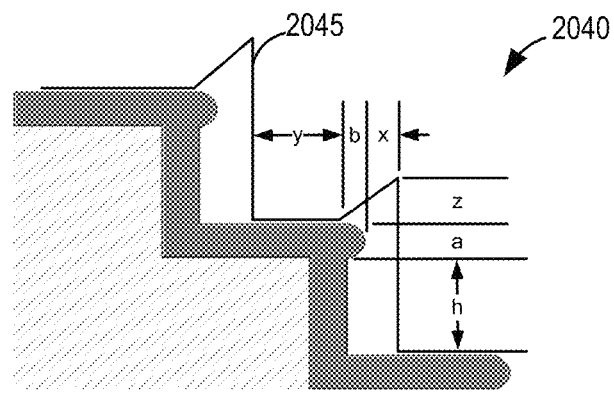
FIG. 20C shows an illustration of an example embodiment of stair guidance determining the dimensions of an invisible fence around a stair nosing.

Referring now to FIGS. 20A, 20B, and 20C, shown therein are illustrations of an example embodiment of stair guidance 2000 for use with a system for gait monitoring and improvement. The stair guidance 2000 may provide stair detection, climbing/descending, and/or cueing. The stair guidance 2000 may be carried out, for example, by system 100.

FIG. 20A shows a first stair type 2010 without nosing and a second stair type 2020 with nosing, side by side. For the first stair type 2010, the system 100 determines a riser height (h) and a stair tread (w). For the second stair type 2020, the system 100 determines a stair nose height (a) and a stair nose width (b).

In FIG. 20B, the system 100 determines a clearance path 2035 around a stair corner. The clearance path 2035 may be visualized as an invisible fence strategically placed around a riser that does not include nosing. The system 100 may use data from the spatial awareness module 340 to determine the foot's position relative to the clearance path 2035. If within the threshold of the clearance path 2035, the system 100 may initiate cueing to guide the wearable device 110 around the clearance path 2035 and up the step. The system 100 may determine the dimensions of the clearance path 2035, for example, using the height of the riser (h), an optimal stair edge vertical clearance (z), an optimal stair edge horizontal clearance (x), and an optimal stair tread coverage (y).

In FIG. 20C, the system 100 determines a clearance path 2045 around a stair nose. The clearance path 2045 may be visualized as an invisible fence strategically placed around a riser that includes nosing. The system 100 may use data from the spatial awareness module 340 to determine the foot's position relative to the clearance path 2045. If within the threshold of the clearance path 2045, the system 100 may initiate cueing to guide the wearable device 110 around the clearance path 2045 and up the step. The system 100 may determine the dimensions of the clearance path 2045, for example, using the height of the riser (h) up to the stair nose, the stair nose height (a), an optimal stair nose vertical clearance (z), an optimal stair nose horizontal clearance (x), the stair nose width (b), and an optimal stair tread coverage (y).

The stair guidance 2000 may be a part of, or incorporated into, method 1600. In that case, the stair guidance 2000 provides some or all of the logic required to determine that the activity type is going up/down stairs (which may also be referred to as "stair ascent/descent").

In at least one embodiment, the stair guidance 2000 is part of a component or functionality of system 100. For example, the stair guidance may loaded onto the microcontroller 115. Alternatively, the stair guidance 2000 may be stored in a module, chip, circuitry, logic, program, or subroutine for use by the microcontroller 115.

Figure 21:
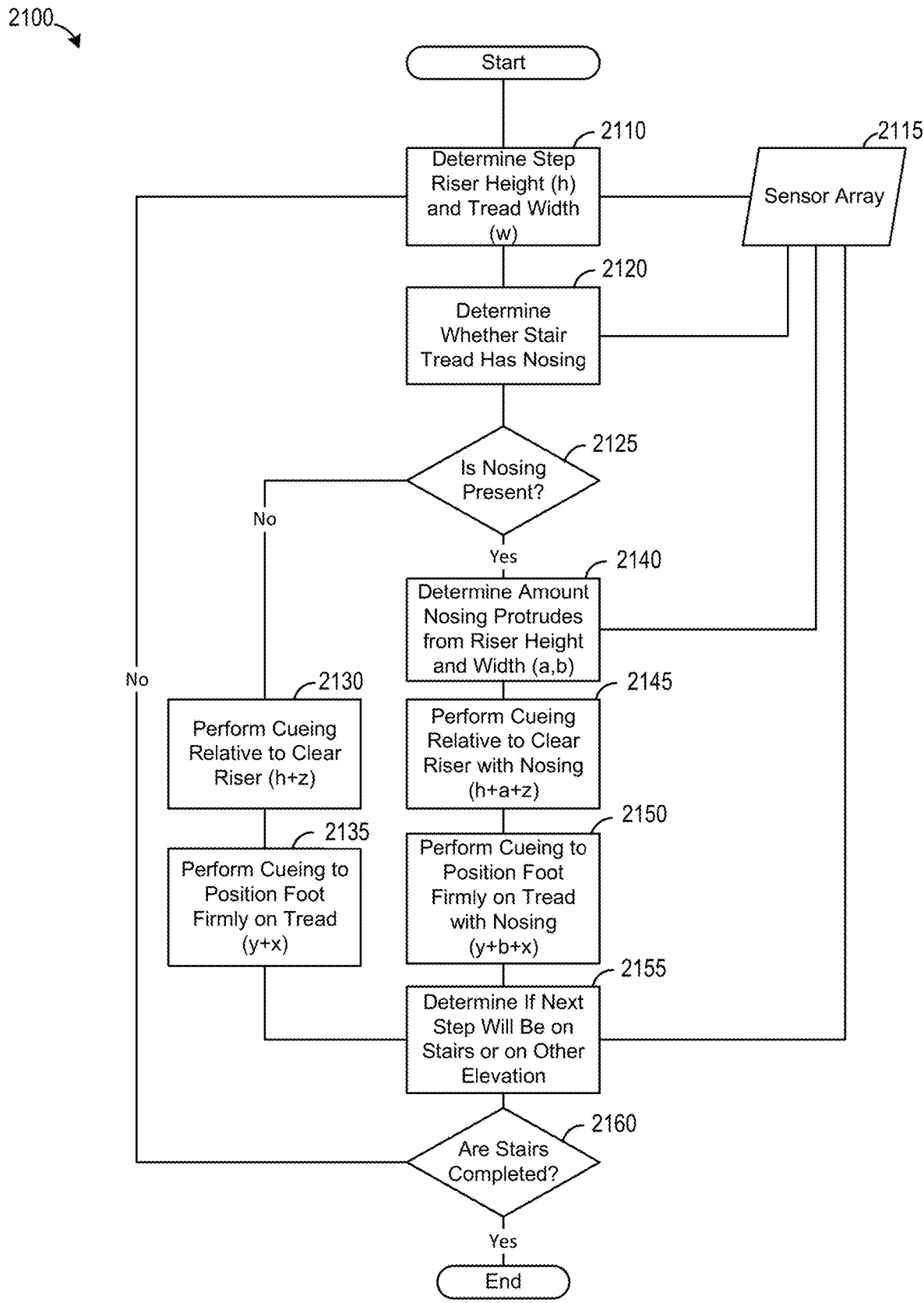
FIG. 21 shows a flow chart of an example embodiment of a method of performing cueing during stair ascension monitoring and improvement.

Referring now to FIG. 21, shown therein is a flow chart of an example embodiment of a method 2100 for performing cueing during stair ascension monitoring and improvement for use with a system for gait monitoring and improvement. Method 2100 may be carried out, for example, by system 100. For illustration purposes, method 2100 may be read in conjunction with the stair guidance 2000 illustrated in FIGS. 20A, 20B, and 20C.

At 2110, the system 100 determines a step riser height (h) and a tread width (w).

At 2115, the system 100 receives data from the sensor array 310.

At 2120, the system 100 determines whether a stair tread has nosing. The system 100 may make this determination, for example, by evaluating data related to spatial awareness.

At 2125, the system 100 determines whether nosing is present. If Yes (i.e., if nosing is present), then the method 2100 proceeds to 2140. If No (i.e., if nosing is absent), then the method 1900 proceeds to 2130.

At 2130, the system 100 performs cueing relative to clear the riser. The system 100 may provide this cueing, for example, by causing the cueing array 360 to activate one of more cueing elements while the wearable device 110 clears the riser by a height of the riser (h) plus an optimal (stair edge) vertical clearance (z).

At 2135, the system 100 performs cueing to position the foot firmly on the tread at the top of the riser. The system 100 may provide this cueing, for example, by causing the cueing array 360 to activate one or more cueing elements while the wearable device 110 moves onto the tread at the top of the riser by a displacement of an optimal (stair edge) horizontal clearance (x) plus an optimal stair tread coverage (y).

At 2140, the system 100 determines an amount that the nosing protrudes from the riser, generating a nose height (a) and a nose width (b).

At 2145, the system 100 performs cueing relative to clear the riser with nosing. The system 100 may provide this cueing, for example, by causing the cueing array 360 to activate one or more cueing elements while the wearable device 110 clears the riser with nosing by a height of the riser (h) plus the height of the nose (a) plus an optimal (stair nose) vertical clearance (z).

At 2150, the system 100 performs cueing to position the foot firmly on the tread at the top of the riser with the nosing. The system 100 may provide this cueing, for example, by causing the cueing array 360 to activate one or more cueing elements while the wearable device 110 moves onto the tread at the top of the riser by a displacement of an optimal (stair nose) horizontal clearance (x) plus the width of the nose (b) plus an optimal stair tread coverage (y).

At 2155, the system 100 determines if a next step will be on stairs or other elevation.

At 2160, the system 100 determines whether the stairs are completed. If Yes (i.e., if the stairs are completed), then the method 2100 ends. If No (i.e., if the stairs are not completed), then the method returns to 2110.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A method for using real-time sensory feedback on a wearable device to improve a patient's gait, the wearable device comprising a microcontroller, a sensor array, a cueing array, and a data store, the method comprising:
   receiving a first data file comprising a baseline active training program to target a mobility abnormality, an active training program comprising a plurality of activity types comprising activity properties defining criteria needed to be met to establish a current activity type from the plurality of activity types, and a behavior modification scheme comprising a cueing response map comprising degrees of correction to improve the patient's gait;
   downloading the baseline active training program and the behavior modification scheme onto the data store;
   receiving sensor data from the sensor array;
   determining the current activity type based at least in part on the sensor data and the activity properties when the current activity type changes from one of the plurality of activity types to another of the plurality of activity types;
   generating cueing intensity feedback by the microcontroller via the cueing array based at least in part on the sensor data, a percentage deviation with reference to the cueing response map, and the current activity type;
   receiving field data from the wearable device generated by the microcontroller, the field data comprising one or more measurable gait parameters;
   dynamically generating a new cueing response map based at least in part on the field data, an analysis of the field data with regards to the current activity type, and a percentage change in deviation with reference to the cueing response map, the degrees of correction of the new cueing response map being modified to further improve the patient's gait; and
   modifying the active training program based at least in part on the cueing response map.

2. The method of claim 1, wherein the analysis of the field data further comprises determining whether the mobility abnormality improved during use of the initial training program in relation to the cueing response map.

3. The method of claim 1, wherein the cueing array comprises a plurality of cueing devices including a first cueing device and a second cueing device, the first cueing device comprising a first position and a first type being one of a lighting device, an auditory device, or a haptic device, the second cueing device comprising a second position and a second type being one of a lighting device, an auditory device, or a haptic device.

4. The method of claim 3, wherein the first type is different from the second type.

5. The method of claim 3, wherein the microcontroller is further configured to generate the cueing intensity feedback by the plurality of cueing devices on the cueing array based at least in part on cueing vector placement comprising dividing cueing vectors into zones and selecting the cueing vectors to provide the cueing intensity feedback corresponding to the behavior modification scheme.

6. The method of claim 1, wherein the activity properties comprise at least one of changes in height, walking cadence parameters, or running cadence parameters.

7. The method of claim 1, wherein the first data file further comprises at least one of a clinician assessment data file relating to the patient's gait and a statistical gait assessment file.

8. The method of claim 1, further comprising generating a recommended training program based at least in part on clinician data.

9. The method of claim 1, wherein the activity type is one of walking, running, ambulating with a mobility aid, going up/down an incline, ascending/descending stairs, idling, performing a custom movement, performing a specialized movement, performing an unknown movement, or transitioning from one activity type to another activity type.

10. The method of claim 1, wherein the criteria is a set of data specific to the activity type sufficient to establish the activity type, the data including at least one of position, velocity, or acceleration.

11. The method of claim 1, further comprising tuning the cueing intensity feedback by the microcontroller based at least in part on a comparison of the sensor data with the percentage deviation with reference to the cueing response map.

12. The method of claim 1, further comprising receiving clinical trial data from the wearable device based at least in part on the cueing intensity feedback.

13. The method of claim 1, further comprising receiving device node data from a device node that is associated with a different body part than the wearable device, where the device node data is related to measurements of movement of the different body part.

14. The method of claim 13, wherein generating the cueing intensity feedback is further based on the device node data, and the method further comprises transmitting the cueing intensity feedback to the device node.

15. The method of claim 1, wherein the wearable device has a form factor of a shoe, the sensor array is disposed within the shoe, and the cueing array is disposed within the shoe.

* * * * *

UNITED STATES PATENT AND TRADEMARK OFFICE
CERTIFICATE OF CORRECTION

PATENT NO. : 11,426,098 B2  
APPLICATION NO. : 16/806716  
DATED : August 30, 2022  
INVENTOR(S) : Matthew Rosato Page 1 of 1

It is certified that error appears in the above-identified patent and that said Letters Patent is hereby corrected as shown below:

In the Claims

Claim 1, Column 24, Line 53, "...part on the cueing response map." should read, -- part on the new cueing response map. --

Signed and Sealed this  
First Day of August, 2023

Katherine Kelly Vidal  
*Director of the United States Patent and Trademark Office*